(12) United States Patent
Harley et al.

(10) Patent No.: US 7,276,341 B2
(45) Date of Patent: Oct. 2, 2007

(54) METHODS AND REAGENTS FOR DIAGNOSIS OF AUTOANTIBODIES

(75) Inventors: John B. Harley, Oklahoma City, OK (US); Judith A. James, Edmond, OK (US)

(73) Assignee: Oklahoma Medical Research Foundation, Oklahoma City, OK (US)

( * ) Notice: Subject to any disclaimer, the term of this patent is extended or adjusted under 35 U.S.C. 154(b) by 17 days.

(21) Appl. No.: 10/376,121

(22) Filed: Feb. 27, 2003

(65) Prior Publication Data

US 2003/0216544 A1 Nov. 20, 2003

Related U.S. Application Data

(60) Division of application No. 07/867,819, filed on Apr. 13, 1992, now Pat. No. 6,897,287, which is a continuation-in-part of application No. 07/648,205, filed on Jan. 31, 1991, now abandoned, which is a continuation-in-part of application No. 07/472,947, filed on Jan. 31, 1990, now abandoned.

(51) Int. Cl.
 G01N 33/53 (2006.01)
 G01N 33/00 (2006.01)
 A61K 38/04 (2006.01)
 C07K 5/00 (2006.01)
 C07K 7/00 (2006.01)
 C07K 16/00 (2006.01)
 C07K 17/00 (2006.01)

(52) U.S. Cl. ................... 435/7.1; 435/7.92; 530/326; 530/327; 530/328; 530/329

(58) Field of Classification Search .............. 435/7.1, 435/7.92; 530/326, 327, 328, 329
 See application file for complete search history.

(56) References Cited

U.S. PATENT DOCUMENTS

| | | | |
|---|---|---|---|
| 4,554,101 | A | 11/1985 | Hopp |
| 4,784,942 | A | 11/1988 | Harley |
| 4,865,970 | A | 9/1989 | Brot et al. |
| 5,312,752 | A | 5/1994 | Wotiz et al. |
| 5,354,691 | A | 10/1994 | Van Eden et al. |

FOREIGN PATENT DOCUMENTS

| | | |
|---|---|---|
| EP | 0 313 156 | 4/1989 |
| WO | WO88/09932 | 12/1988 |
| WO | WO91/11718 | 8/1991 |
| WO | WO91/17171 | 11/1991 |
| WO | WO94/02445 | 2/1994 |
| WO | WO94/02509 | 2/1994 |

OTHER PUBLICATIONS

The Merck Manual of Diagnosis and therapy, vol. 17, 1999.*
James, J.A. and J.B. Hartley. 'Sequential Epitopes of an Sm B/B' Protein.' Arthritis and Rheumatism. 34(9): S133, 1991.*

Alexander, et al., "Anti-Ro/SS-A antibodies in the pathophysiolgy of congenital geart block in neonatal lupus syndrome, an experimental model," Arth. Rheum. 35: 176-189 (1992).
Alspaugh, et al., "Differentiation and characterization of autoantibodies and their antigens in Sjogren's syndrome," Arthr. Rheum. 19: 216-222 (1976).
Bachmann, et al., "Characterization of the autoantigen La as a nucleic acid-dependent ATPase/dATPase with melting properties," Cell 60: 85-93 (1990).
Banerjee, et al., "Complete nucleotide sequence of the mRNA coding for the N protein of vesicular stomatitis virus (New Jersey Serotype)," Virology 137:432-438 (1984).
Barakat, et al., "Recognition of synthetic peptides of Sm-D autoantigen bu lupus sera," Clin. Exp. Immunol. 81: 256-262 (1990).
Barakat, et al., "IgG antibodies from patients with primary Sjogren's syndrome and systemic lupus erythematosus recognize different epitopes in 60-kD SSA/Ro protein," Clin. Exp. Immunol. 89: 38-45 (1992).
Ben-Chetrit, et al., "Isolation and characterization of a cDNA encoding the 60-kD component of the human SS-A/Ro ribonucleoprotein autoantigen," J. Clin. Inv. 83: 1284-1292 (1989).
Bernstein, et al., "Cellular protein and RNA antigens in autoimmune disease," Mol. Biol. Med. 2: 105-120 (1984).
Blank, et al., "Induction of experimental anti-phospholipid syndrome associated with SLE following immunization with human monoclonal pathogenic anti-DNA idiotype," J. Autoimmunity 5: 495-509 (1992).
Blank, et al., "Induction of SLE-like disease in naive mice with a monoclonal anti-DNA antibody derived from a patient with polymyositis carrying the 16/6 Id," J. Autoimmunity 1: 683-691 (1988).
Blank, et al., "Induction of systemic lupus erythematosus in naive mice with T-cell lines specific for human anti-DNA antibody SA-1 (16/6 Id+)," Clin. Immunol. Immunopathol. 60: 471-483 (1991).
Blank, et al., "Sex hormone involvement in the induction of experimental systemic lupus erythematosus by a pathogenic anti-DNA idiotype in naive mice," J. Rheumatol. 17: 311-317 (1990).
Blank, et al., "The effect of the immunomodulator agent AS101 on interleukin-2 production in synthetic lupus erythematosus (SLE) induced in mice by a pathogenic anti-DNA antibody," Clin. Exp. Immunol. 79: 443-447 (1990).

(Continued)

Primary Examiner—Maher M. Haddad
Assistant Examiner—Nora M. Rooney
(74) Attorney, Agent, or Firm—Fulbright & Jaworski, LLP

(57) ABSTRACT

A number of octapeptides were generated from the sequences encoding the 60 kDa Ro/SSA peptide, the La/SSB autoantigen, the 70 kD nuclear ribonucleoprotein (nRNP), and the Sm B/B' polypeptide, which represent linear epitopes for autoantibodies present in the sera of SLE and SS patients. These peptides are useful in solid phase assays for patients characterized by the presence of these autoantibodies, and can be used to categorize patients as to the likelihood of developing certain conditions associated with SLE. The peptides are also potentially useful in treatment of these patients using immobilized peptide to remove autoantibody and to block binding of the autoantibodies with patient molecules reactive with the autoantibodies.

4 Claims, 3 Drawing Sheets

OTHER PUBLICATIONS

Buyon, "Neonatal lupus syndromes," Curr. Opin. in Rhuem. 6: 523-529 (1994).
Chambers, et al., "Genomic structure and amino acid sequence domains of the human La autoantigen," J. Biol. Chem. 263: 18043-18051 (1988).
Chambers & Keene, "Isolation and analysis of cDNA clones expressing human lupus La antigen," Proc. Natl. Acad. Sci. USA 82: 2115-2119 (1985).
Chan, et al., "Ribonucleoprotein SS-B/La belongs to a protein family with consensus sequences for RNA-binding," Nucl. Acids Res. 17: 2233-2244 (1989).
Cohen, "The self, the world and autoimmunity," Scientific American 258: 52-60 (1988).
Colman, "Effects of amino acid sequence changes on antibody-antigen interactions," Res. Immunol. 145: 33-36 (1994).
Craft, et al., "Murine and drosophila B proteins of SM snRNPS," Mol. Biol. Rep. 15: 159 (1991).
Depolo, et al., "Continuing coevolution of virus and defective interfering particles and of viral genome sequences during undiluted passages: virus mutants exhibiting nearly complete resistance to formerly dominant defective interfering particles," J.Virology 61: 454-464 (1987).
Deutscher, et al., "Molecular analysis of the 60-kDa human Ro ribonucleoprotein," Proc. Natl. Acad. Sci. USA 85: 9479-9483 (1988).
Dickey, "Human autoantibody producing grafts in SCID mice," presented to the Oklahoma Lupus Association, Sep. 1989 (abstract).
Dyrberg, et al., "Peptides as probes to study molecular mimicry and virus-induced autoimmunity," Current Topics in Microbiol. 130: 25-37 (1986).
Elkon, et al., "Epitope mapping of recombinant HeLa SmB and B[1] peptides obtained by the polymerase chain reaction," J. Immun. 145: 636-643 (1990).
Esquivel, et al., "Induction of autoimmunity in good and poor responder mice with mouse thyrobglobulin and lipopolysaccharide," J. Exp. Med. 145: 1250-1263 (1977).
Ferris & Donaldson, "An enzyme-linked immunosorbent assay for the detection of vesicular stomatitis virus antigen," Vet. Biol. 18(3-4): 243-258 (1988).
Fisher, "Temporal shifts from Sm to ribonucleoprotein reactivity in systemic lupus erythematosus," Arthritis Rheum. 28: 1348 (1985).
Fricke, et al., "Induction of experimental systemic lupus erythematosus in mice by immunization with monoclonal anti-La autoantibody," Intern. Immunol. 2: 225-230 (1990).
Fritz, et al., "Small nuclear U-ribonucleoproteins in *Xenopus laevis* development," J. Mol. Biol. 178: 273-285 (1984).
Gaither, et al., "Affinity purification and immunoassay of anti-Ro/SSA," Protides Biol. Fluids 33: 413-416 (1985).
Gallione, et al., "Nucleotide sequences of the mRNA's encoding the vesicular stomatitis virus N and NS proteins," Virology 39: 529-535 (1981).
Geysen, et al., "Strategies for epitope analysis using peptide synthesis," J. Immun. Methods 102: 259-271 (1987).
Geysen, et al., "Use of peptide synthesis to probe viral antigens for epitopes to a resolution of a single amino acid," Proc. Natl. Acad. Sci. USA 81: 3998-4002 (1984).
Gottlieb & Steitz, "The RNA binding protein La influences both the accuracy and the efficiency of RNA polymerase III transcription in vitro," EMBO J. 8: 841 (1989).
Guldner, et al., "Epitope mapping with a recombinant human 68-kDa (U1) ribonucleoprotein antigen reveals heterogenous autoantibody profiles in human autoimmune sera," J. Immunol. 141(2): 469-475 (1988).
Habets, et al., "Characterization of the SS-B (La) antigen in adenovirus infected and uninfected HeLa cells," EMBO J. 2: 1625 (1983).
Harley, et al., "Anti-Ro (SS-A) and Anti-La (SS-B) in patients with Sjogren's Syndrome," Arthritis Rheum. 29: 196-206 (1986).
Harley & Gaither, Autoantibodies. In Rheumatic Disease Clinics of North American: Systemic Lupus Erythematosus, 14: 43-56 (1988).
Harley, et al., Arthritis Rheum. 28: 1321-1325 (1985).
Herbert, et al., Dictionary of Immunology, 3rd Ed., Blackwell Scientific Publications: Oxford, UK, p. 14 (1995).
Hinterberger, et al., "Isolation of small nuclear ribonucleoproteins containing U1, U2, U4, U5 and U6 RNAs," J. Biol. Chem. 258: 2604-2613 (1983).
Horsfall, et al., "Ro and La antigens and maternal Anti-La idiotype on the surface of myocardial fibres in congenital heart block," J. Autoimmunity 4: 165-176 (1991).
Horsfall, et al., "Purification of human autoantibodies from cross-linked antigen immunosorbents," J. Immunol. Meth. 104: 43-49 (1987).
Huang, et al., "Human Anti-Ro autoantibodies bind peptides accessible to the surface of the native Ro autoantigen," Scand. J. Immunol. 41: 220-228 (1995).
Huang, et al., "Immunization with vesicular stomatitis virus nucleocapsid protein induces autoantibodies to the 60 kD Ro ribonucleoprotein particle," J. Investig. Med. 43: 151-158 (1995).
James & Harley, "Human lupus anti-spliceosome A autoantibodies bind contiguous surface structures and segregate into two sequential epitope binding patterns," J. Immunol. 156(10): 4059-4066 (1996).
James & Harley, "Peptide autoantigenicity of the small nuclear ribonucleoprotein C," Clin. Exp. Rheum. 13: 299-305 (1995).
James & Harley, "Sequential fine specificity of the small nuclear ribonuclear protein C," Clinical Res. 41(2): PA393 (1993).
James, et al., "Basic amino acids predominate in the sequential autoantigenic determinants of the small nuclear 70K ribonucleoprotein," Scand. J. Immunol. 39: 557-566 (1994).
James, et al., "Immunoglobulin epitope spreading and autoimmune disease after peptide immunization: Sm B/B[1]-derived PPPGMRPP and PPPGIRGP induce sliceosome autimmunity," J. Exp. Med. 181: 453-461 (1995).
James, et al., "Linear epitope mapping of an Sm B/B[1] polypeptide," J. Immunol. 148: 2074-2079 (1992).
James, et al., "Sequential autoantigenic determinants of the small nuclear ribonucleoprotein Sm D shared by human lupus autoantibodies and MRL 1pr/1pr antibodies," Clin. Exp. Immunol. 98: 419-426 (1994).
Kaliyaperumal, et al., "Nucleosomal peptide epitopes for nephritis-inducing T helper cells of murine lupus," J. Exp. Med. 183: 2459-2469 (1996).
Kalush, et al., "Neonatal lupus erythematosus with cardiac involvement in offspring of mothers with experimental systemic lupus erythematosus," J. Clin. Immunol. 14: 314-321 (1994).
Kyte & Doolittle, "A simple method for displaying the hydropathic character of a protein," J. Mol. Biol. 157: 105-132 (1982).
Lee, et al., "Cardiac immunoglobulin deposition in congenital heart block associated with maternal anti-Ro autoantibodies," Am. J. Med. 83: 793-796 (1987).
Lee, et al., "Pattern of cutaneous immunoglobulin G deposition in subacute cutaneous lupus erythematosus is reproduced by infusing purified anti-Ro (SSA) autoantibodies into human skin-grafted mice," J. Clin. Invest. 83: 1556-1562 (1989).
Lehmann, et al., "Spreading of T-cell autoimmunity to cryptic determinants of an autoantigen," Nature 356: 155-157 (1992).
Lerner, et al., "Are snRNPs involved in splicing?" Nature 283: 220-224 (1980).
Lerner & Steitz, "Antibodies to small nuclear RNAs complexed with proteins are produced by patients with systemic lupus erythematosus," Proc. Natl. Acad. Sci. USA 76: 5495 (1979).
Maddison, et al., "Quantification of precipitating antibodies to certain soluble nuclear antigens in SLE," Arthritis Rheum. 20: 819-824 (1977).
Maddison & Reichlin, "Deposition of antibodies to a soluble cytoplasmic antigen in the kidneys of patients with systemic lupus erythematosus," Arthrtis Rheum. 22: 858-863 (1979).
Manfredi, et al., "Molecular anatomy of an autoantigen: T and B epitopes on the nicotinic acetylcholine receptor in myasthenia gravis," J. Lab. Clin. Med. 120: 13-21 (1992).
Maniatis & Reed, "The role of small nuclear ribonucleoprotein particles in pre-mRNA splicing," Nature 325: 673-678 (1987).
Matter, et al., "Molecular characterization of ribonucleoprotein antigens bound by antinuclear antibodies," Arthritis Rheum. 25: 1278-1283 (1983).

Mattioli, et al., "Physical association of two nuclear antigens and mutual occurrence of their antibodies: The relationship of the SM and RNA Protein (MO) systems in SLE sera," J. Immunol. 110: 1318-1324 (1973).

Mattioli & Reichlin, "Heterogeneity of RNA protein antigens reactive with sera of patients with systemic lupus erythematosus. Description of a cytoplasmic nonribosomal antigen," Arthritis Rheum. 17: 421-429 (1974).

McAlister, et al., "cDNA sequences of the rat U snRNP-associated protein N: description of a potential Sm epitope," EMBO J. 8: 1177-1181 (1989).

McCauliffe, et al., "Molecular cloning, expression, and chromosome 19 localization of a human Ro/SS-A autoantigen," J. Clin. Invest. 85: 1379-1391 (1990).

Mendlovic, et al., "Induction of an SLE-like disease in mice by a common anti-DNA idiotype," Proc. Natl. Acad. Sci. USA 85: 2260-2264 (1988).

Mendlovic, et al., "The genetic regulation of the induction of experimental SLE," Immunology 69: 228-236 (1990).

Mendlovic, et al., "The role of anti-idiotypic antibodies in the induction of experimental systemic lupus erythematosus in mice," Eur. J. Immunol. 19: 729-732 (1989).

Miller, et al., "The role of autoantigen, histidyl-tRNA synthetase, in the induction and maintenance of autoimmunity," Proc. Natl. Acad. Sci. USA 87: 9933-9937 (1990).

Mosier, et al., "Transfer of a functional human immune system to mice with severe combined immunodeficiency," Nature 335: 256-259 (1988).

Munves, et al., "Antibodies to Sm and RNP," Arthritis Rheum. 26: 848-853 (1983).

Ohosone, et al., "Molecular cloning of cDNA encoding Sm autoantigen: derivation of a cDNA for a B polypeptide of the U series of small nuclear ribonucleoprotein particles," Proc. Natl. Acad. of Sci. USA 86: 4249-4253 (1989).

Palfi, et al., "Purification of the major UsnRNPs from broad bean nuclear extracts and characterization of their protein constitutants," Nuceic Acids Res. 17: 1445-1458 (1989).

Penner & Reichlin, "Primary billary cirrhosis associated with Sjogren's syndrome: evidence for circulating and tissue-deposited Ro/anti-Ro immune complexes," Arthritis Rheum. 25: 1250-1253 (1982).

Query, et al., "A common RNA recognition motif identified within a defined U1 RNA binding of the 70K U1 snRNP protein," Cell 57: 89-101 (1989).

Reichlin, et al., "Autoantibodies to the URNP particles: relationship to clinical diagnosis and nephritis," Clin. Exp. Immunol. 83: 286-290 (1991).

Reichlin, et al., "Concentration of autoantibodies to native 60-kd Ro/SS-A and denatured 52-kd Ro/SS-A in eluates from the heart of a child who died with congenital complete heart block," Arth. Rheum. 37: 1698-1703 (1994).

Renz, et al., "Expression of the major human ribonucleoprotein (RNP) autoantigens in *Escherichia coli* and their use in an EIA for screening sera from patients with autoimmune diseases," Clin. Chem. 35: 1861-1863 (1989).

Rokeach, et al., "Primary structure of a human small nuclear ribonucleoprotein polypeptide as deducted by cDNA analysis," J. Biol. Chem. 264: 5024-5030 (1989).

Rokeach, et al., "Molecular cloning of a cDNA encoding the Sm-D autoantigen,"Proc. Natl. Acad. Sci. USA 85: 4832-4836 (1988).

Rose, et al., "Genetic regulation in autoimmune thyroiditis," in Autoimmunolgy Genetic, Immunologic Virologic, and Clinical Aspects (Talal, ed.) Academic Press: New York, pp. 63-87 (1977).

Rose, et al., "Studies on experimental thyroiditis," Ann. NY Acad. Sci. 124: 201-208 (1965).

Rose, et al., "T-cell regulation in autoimmune thyroiditis," Immunol. Reviews 55: 229-314 (1981).

Schaack, Ann. Int. Med. 111(7): 581-591 (1989).

Schmauss, et al., "A comparison of snRNP-associated Sm-autoantigens: human N, rat N and human B/B[1]," Nucl. Acids Res. 17: 1733-1734 (1989).

Scofield & Harley, "Autoantigenicity of Ro/SSA antigen is related to a nucleocapsid protein of vesicular stomatitis virus," Proc. Natl. Acad. Sci. USA 88: 3343-3347 (1991).

Sharp, "Splicing of messenger RNA precursors," Science 235: 766-771 (1987).

Sharpe, "Isolation of cDNA clones encoding the human Sm B/B[1] auto-immune antigen and specifically reacting with human anti-Sm auto-immune sera," FEBS Letters 250(2): 585-590 (1989).

Shoenfeld, et al., "Pathogenic idiotypes of autoantibodies in autoimmunity: lessons from new experimental modes of SLE," FASEB J. 4: 2646-2651 (1990).

Shoenfeld, "Modulation of experimental SLE induced in naive mice by a pathogenic anti-DNA idiotype (16/6 Id.)," Proceedings of the Second International conference on Systemic Lupus Erythematosus, Tokyo, Japan Professional Postgraduate Services 93 (1989).

Sillekens, et al., "cDNA cloning of the human U1 snRNA-associated A protein: extensive homology between U1 and U2 snRNP-specific proteins," EMBO J. 6: 3841-3848 (1987).

Sillekens, et al., "Human U1 snRNP-specific C protein: complete cDNA and protein sequence and identification of a multigene family in mammals," Nucl. Acids. Res. 16: 8307-8321 (1988).

Spritz, et al., "The human U1-70K sn RNP protein: cDNA cloning, chromosomal localization, expression, alternative splicing and RNA-binding," Nucl. Acids Res. 15: 10373-10391 (1987).

Steitz, et al., "Small ribonucleoproteins from eukaryotes: structures and roles in RNA biogenesis," Cold Spring Harbor Symposium Quant. Biol. 47: 893-900 (1983).

Stefano, "Purified lupus antigen La recognizes an oligouridylate stretch common to the $3^1$ termini of RNA polymerase III transcripts," Cell 36: 145-154 (1984).

Sturgess, et al., "Characteristics and epitope mapping of a cloned human autoantigen La," J. Immunol. 140: 3212-3218 (1988).

Tan, et al., "Characterization of a soluble nuclear antigen precipitating with sera of patients with systemic lupus erythematosus," J. Immunol. 96: 464-471 (1966).

Tan, et al., "The 1982 revised criteria for the classification of systemic lupus erythematosus," Arthritis Rheum. 25: 1271-1277 (1982).

The Medical Letter on Drugs and Thereapeutics 37(951):55-57 (Jun. 23, 1995).

Theissen, et al., "Cloning of the human cDNA for the U1 RNA-associated 70K protein," EMBO J. 5: 3209-3217 (1986).

Tigbe, "Production of human reumatoid factors (RF) by SCID mice transplanted with synovial membrane lymphocytes," presented at the Arthritis Foundation Fellows Conference, Amelia Island Plantation, Florida, Dec. 8-10, 1989.

Tincani, et al., "Induction of experimental SLE in naive mice by immunization with human polyclonal anti-DNA antibody carrying the 16/6 idiotypic," Clin. Exp. Rheum. 11: 129-134 (1993).

Tisch, et al., "Antigen-specific immunotherapy: is it a real possibility to combat T-cell-mediated autoimmunity?" Proc. Natl. Acad. Sci. USA 91: 437-438 (1994).

Tzartos, et al., "The main immunogenic region of the acetylcholine receptor. Structure and role in myasthenia gravis," Autoimmunity 8: 259-270 (1991).

Van Dam, et al., "Cloned human snRNP proteins B and B[1] differ only in their carboxy-terminal part," EMBO J. 8: 3853-3860 (1989).

Venables, et al., "Purification and characterization of the Sjogren's syndrome A and B antigens.," Clin. Exp. Immunol. 54: 731-738 (1983).

Virji, et al., "Location of a blocking epitope on outer-membrane protein III of *Neisseria gonorrhoeae* by synthetic peptide analysis," J. Gen. Microbiol. 135(7): 1895-1899 (1989).

Voller, et al., "Enzyme-linked immunosorbent assay," in Manual of Clinical Laboratory Immunology, Chapt. 17 (1986).

Waite, et al., "Anti-Jo-1 antibodies are directed at an evolutionary-conserved, conformational site on human histidyl-tRNA synthetase," Mol. Cell Biol. Autoantibodies Autoimm. 100-101 (1989).

Waltuck & Buyon, "Autoantibody-associated congenital heart block: outcome in mothers and children," Ann. Intern. Med. 120: 544-551 (1994).

Watson, et al., "Certain properties make substances antigenic," in Molecular Biology of the Gene, 4th Ed., Benjamin/Cummings Publishing Co.: Melano Park, p. 836 (1987).

Williams, et al., "A repeated Proline-rich sequence in Sm B/B[1] and N is a dominant epitope recognized by human and murine autoantibodies," J. Am. Med. Assoc. 164: 1439-1447 (1957).

Wraith, et al., "Antigen recognition in autoimmune encephalomyelitis and the potential for peptide-mediated immunotherapy," Cell 59: 247-255 (1989).

Yamamoto, et al., "Isolation and characterization of a complementary DNA expression human U1 small nuclear ribonucleoprotein C polypeptide," J. Immun. 140: 311-317 (1988).

Zeller, et al., "Nucleocytoplasmic distribution of snRNPs and stockpiled snRNA-binding proteins during oogenesis and early development in *Xenopus laevis*," Cell 32: 425-434 (1983).

\* cited by examiner

```
                        SEQUENCE LISTING (1) GENERAL INFORMATION:

(iii) NUMBER OF SEQUENCES: 218

(2) INFORMATION FOR SEQ ID NO: 1:

(i) SEQUENCE CHARACTERISTICS:
           (A) LENGTH: 8 amino acids
           (B) TYPE: amino acid
           (C) STRANDEDNESS: single
           (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
           (A) ORGANISM: Homo sapiens (ix) FEATURE:
           (A) NAME/KEY: Binding-site
           (B) LOCATION: 1..8

(x) PUBLICATION INFORMATION:
           (A) AUTHORS: Harley, John B.

(xi) SEQUENCE DESCRIPTION: SEQ ID NO: 1:

Gly Thr Phe Lys Ala Phe Asp Lys
1               5

(2) INFORMATION FOR SEQ ID NO: 2:

(i) SEQUENCE CHARACTERISTICS:
           (A) LENGTH: 15 amino acids
           (B) TYPE: amino acid
           (C) STRANDEDNESS: single
           (D) TOPOLOGY: linear (ii) MOLECULE TYPE: peptide (ix) FEATURE:
           (A) NAME/KEY: Binding-site
           (B) LOCATION: 1..8

(xi) SEQUENCE DESCRIPTION: SEQ ID NO: 2:

Cys Asp Glu Phe Arg Lys Ile Lys Pro Lys Asn Ala Lys Gln Pro
1               5                  10                  15

(2) INFORMATION FOR SEQ ID NO: 3:

(i) SEQUENCE CHARACTERISTICS:
           (A) LENGTH: 8 amino acids
           (B) TYPE: amino acid
           (C) STRANDEDNESS: single
           (D) TOPOLOGY: linear
```

-continued

```
    (ii) MOLECULE TYPE: peptide (ix) FEATURE:
         (A) NAME/KEY: Binding-site
         (B) LOCATION: 1..8

(xi) SEQUENCE DESCRIPTION: SEQ ID NO: 3:

Arg Val Pro Leu Ala Gly Ala Ala
1               5

(2) INFORMATION FOR SEQ ID NO: 4:

(i) SEQUENCE CHARACTERISTICS:
         (A) LENGTH: 17 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Binding-site
         (B) LOCATION: 4..11

(xi) SEQUENCE DESCRIPTION: SEQ ID NO: 4:

Ala Gly Gly Pro Gly Val Gly Arg Ala Ala Gly Arg Gly Val Pro
1               5                   10                  15

Ala Gly (2)NFORMATION FOR SEQ ID NO: 5:

(i) SEQUENCE CHARACTERISTICS:
         (A) LENGTH: 15 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Binding-site
         (B) LOCATION: 7..14

(xi) SEQUENCE DESCRIPTION: SEQ ID NO: 5:

Ala Gly Leu Ala Gly Pro Val Arg Gly Val Gly Gly Pro Ser Gln
1               5                   10                  15

(2) INFORMATION FOR SEQ ID NO: 6:

(i) SEQUENCE CHARACTERISTICS:
         (A) LENGTH: 12 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Binding-site
         (B) LOCATION: 3..10

(xi) SEQUENCE DESCRIPTION: SEQ ID NO: 6:

Gln Val Met Thr Pro Gln Gly Arg Gly Thr Val Ala
1               5                   10

(2) INFORMATION FOR SEQ ID NO: 7:

(i) SEQUENCE CHARACTERISTICS:
         (A) LENGTH: 15 amino acids
         (B) TYPE: amino acid
```

```
        (C) STRANDEDNESS: single
        (D) TOPOLOGY: linear (ii) MOLECULE TYPE: peptide (ix) FEATURE:
        (A) NAME/KEY: Binding-site
        (B) LOCATION: 8..15

(xi) SEQUENCE DESCRIPTION: SEQ ID NO: 7:

Pro Thr Gln Tyr Pro Pro Gly Arg Gly Thr Pro Pro Pro Val
1               5                  10                  15

(2) INFORMATION FOR SEQ ID NO: 8:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Binding-site
        (B) LOCATION: 2..9

(xi) SEQUENCE DESCRIPTION: SEQ ID NO: 8:

Thr Pro Pro Pro Pro Val Gly Arg Ala Thr Pro Pro Gly Ile
1               5                  10                  15

(2) INFORMATION FOR SEQ ID NO: 9:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Binding-site
        (B) LOCATION: 1..8

(xi) SEQUENCE DESCRIPTION: SEQ ID NO: 9:

Pro Pro Pro Gly Ile Met Ala Pro
1               5

(2) INFORMATION FOR SEQ ID NO: 10:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Binding-site
        (B) LOCATION: 3..10

(xi) SEQUENCE DESCRIPTION: SEQ ID NO: 10:

Met Ala Pro Pro Pro Gly Met Arg Pro Pro Met
1               5                  10

(2) INFORMATION FOR SEQ ID NO: 11:

(i) SEQUENCE CHARACTERISTICS:
        (A) LENGTH: 16 amino acids
```

```
        (B) TYPE: amino acid
        (C) STRANDEDNESS: single
        (D) TOPOLOGY: linear (ii) MOLECULE TYPE: peptide (ix) FEATURE:
        (A) NAME/KEY: Binding-site
        (B) LOCATION: 5..12

(xi) SEQUENCE DESCRIPTION: SEQ ID NO: 11:

Pro Ile Gly Leu Pro Pro Ala Arg Gly Thr Pro Ile Gly Met Pro
1               5                  10                  15

Pro (2)NFORMATION FOR SEQ ID NO: 12:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Binding-site
        (B) LOCATION: 1..8

(xi) SEQUENCE DESCRIPTION: SEQ ID NO: 12:

Pro Ile Gly Met Pro Pro Pro Gly
1               5

(2) INFORMATION FOR SEQ ID NO: 13:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Binding-site
        (B) LOCATION: 1..8

(xi) SEQUENCE DESCRIPTION: SEQ ID NO: 13:

Arg Pro Pro Pro Pro Gly Ile Arg Gly Pro Pro
1               5                  10

(2) INFORMATION FOR SEQ ID NO: 14:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Binding-site
        (B) LOCATION: 3..10

(ix) FEATURE:
        (A) NAME/KEY: Misc Feature
        (B) LOCATION: 9
        (D) OTHER INFORMATION: /note= "The Xaa at position 9 can be
            R, F, G, H, I, K, S, T, V,
            and Y."
```

(xi) SEQUENCE DESCRIPTION: SEQ ID NO: 14:

Arg Gly Pro Pro Pro Pro Gly Met Xaa Pro Pro Arg
1               5                   10

(2) INFORMATION FOR SEQ ID NO: 15:

(i) SEQUENCE CHARACTERISTICS:
       (A) LENGTH: 9 amino acids
       (B) TYPE: amino acid
       (C) STRANDEDNESS: single
       (D) TOPOLOGY: linear (ii) MOLECULE TYPE: peptide (ix) FEATURE:
       (A) NAME/KEY: Binding-site
       (B) LOCATION: 1..8

(xi) SEQUENCE DESCRIPTION: SEQ ID NO: 15:

Thr Phe Lys Ala Phe Asp Lys His Met
1               5

(2) INFORMATION FOR SEQ ID NO: 16:

(i) SEQUENCE CHARACTERISTICS:
       (A) LENGTH: 8 amino acids
       (B) TYPE: amino acid
       (C) STRANDEDNESS: single
       (D) TOPOLOGY: linear (ii) MOLECULE TYPE: peptide (ix) FEATURE:
       (A) NAME/KEY: Binding-site
       (B) LOCATION: 1..8

(xi) SEQUENCE DESCRIPTION: SEQ ID NO: 16:

Glu Gly Pro Pro Pro Lys Asp Thr
1               5

(2) INFORMATION FOR SEQ ID NO: 17:

(i) SEQUENCE CHARACTERISTICS:
       (A) LENGTH: 8 amino acids
       (B) TYPE: amino acid
       (C) STRANDEDNESS: single
       (D) TOPOLOGY: linear (ii) MOLECULE TYPE: peptide (ix) FEATURE:
       (A) NAME/KEY: Binding-site
       (B) LOCATION: 1..8

(xi) SEQUENCE DESCRIPTION: SEQ ID NO: 17:

Lys Asp Thr Gly Ile Ala Arg Val
1               5

(2) INFORMATION FOR SEQ ID NO: 18:

(i) SEQUENCE CHARACTERISTICS:
       (A) LENGTH: 10 amino acids
       (B) TYPE: amino acid
       (C) STRANDEDNESS: single
       (D) TOPOLOGY: linear (ii) MOLECULE TYPE: peptide (ix) FEATURE:
       (A) NAME/KEY: Binding-site
       (B) LOCATION: 3..10

```
        (xi) SEQUENCE DESCRIPTION: SEQ ID NO: 18:

Ile Pro Gln Ala Pro Ala Gly Leu Ala Gly
1               5                   10

(2) INFORMATION FOR SEQ ID NO: 19:

(i) SEQUENCE CHARACTERISTICS:
           (A) LENGTH: 18 amino acids
           (B) TYPE: amino acid
           (C) STRANDEDNESS: single
           (D) TOPOLOGY: linear (ii) MOLECULE TYPE: peptide (ix) FEATURE:
           (A) NAME/KEY: Binding-site
           (B) LOCATION: 4..16

(xi) SEQUENCE DESCRIPTION: SEQ ID NO: 19:

Gln Val Leu Asn Ile Gln Met Arg Arg Thr Leu His Lys Ala Phe
1               5                   10                  15

Lys Gly Ser (2)NFORMATION FOR SEQ ID NO: 20:

(i) SEQUENCE CHARACTERISTICS:
           (A) LENGTH: 21 amino acids
           (B) TYPE: amino acid
           (C) STRANDEDNESS: single
           (D) TOPOLOGY: linear (ii) MOLECULE TYPE: peptide (ix) FEATURE:
           (A) NAME/KEY: Binding-site
           (B) LOCATION: 8..15

(xi) SEQUENCE DESCRIPTION: SEQ ID NO: 20:

Ile Cys His Gln Ile Glu Tyr Tyr Phe Gly Asp Phe Asn Leu Pro
1               5                   10                  15

Arg Asp Lys Phe Leu Lys
                20

(2) INFORMATION FOR SEQ ID NO: 21:

(i) SEQUENCE CHARACTERISTICS:
           (A) LENGTH: 12 amino acids
           (B) TYPE: amino acid
           (C) STRANDEDNESS: single
           (D) TOPOLOGY: linear (ii) MOLECULE TYPE: peptide (ix) FEATURE:
           (A) NAME/KEY: Binding-site
           (B) LOCATION: 2..9

(xi) SEQUENCE DESCRIPTION: SEQ ID NO: 21:

Trp Val Pro Leu Glu Ile Met Ile Lys Phe Asn Arg
1               5                   10

(2) INFORMATION FOR SEQ ID NO: 22:

(i) SEQUENCE CHARACTERISTICS:
           (A) LENGTH: 12 amino acids
           (B) TYPE: amino acid
           (C) STRANDEDNESS: single
           (D) TOPOLOGY: linear
```

```
    (ii) MOLECULE TYPE: peptide (ix) FEATURE:
         (A) NAME/KEY: Binding-site
         (B) LOCATION: 3..10

(xi) SEQUENCE DESCRIPTION: SEQ ID NO: 22:

Lys Thr Lys Ile Arg Arg Ser Pro Ser Lys Pro Leu
1               5                   10

(2) INFORMATION FOR SEQ ID NO: 23:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (ix) FEATURE:
         (A) NAME/KEY: Binding-site
         (B) LOCATION: 1..8

(xi) SEQUENCE DESCRIPTION: SEQ ID NO: 23:

Asn Arg Leu Asn Arg Leu Thr Thr Asp Phe Asn Val Ile Val Glu
1               5                   10                  15

(2) INFORMATION FOR SEQ ID NO: 24:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (ix) FEATURE:
         (A) NAME/KEY: Binding-site
         (B) LOCATION: 4..13

(xi) SEQUENCE DESCRIPTION: SEQ ID NO: 24:

Gly Glu Ile Lys Trp Ile Asp Phe Val Arg Gly Ala Lys
1               5                   10

(2) INFORMATION FOR SEQ ID NO: 25:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (ix) FEATURE:
         (A) NAME/KEY: Binding-site
         (B) LOCATION: 6..13

(xi) SEQUENCE DESCRIPTION: SEQ ID NO: 25:

Ser Leu Asn Lys Trp Lys Ser Lys Gly Arg Arg Phe Lys Gly Lys
1               5                   10                  15
Gly Lys Gly Asn Lys
                20

(2) INFORMATION FOR SEQ ID NO: 26:

(i) SEQUENCE CHARACTERISTICS:
```

```
            (A) LENGTH: 12 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Binding-site
            (B) LOCATION: 5..12

(xi) SEQUENCE DESCRIPTION: SEQ ID NO: 26:

Gly Asn Leu Gln Leu Arg Asn Lys Glu Val Thr Trp
1               5                   10

(2) INFORMATION FOR SEQ ID NO: 27:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Binding-site
            (B) LOCATION: 2..9

(xi) SEQUENCE DESCRIPTION: SEQ ID NO: 27:

Ile Phe Val Val Phe Asp Ser Ile Glu
1               5

(2) INFORMATION FOR SEQ ID NO: 28:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Binding-site
            (B) LOCATION: 7..14

(xi) SEQUENCE DESCRIPTION: SEQ ID NO: 28:

Lys Glu Thr Asp Leu Leu Ile Leu Phe Lys Asp Asp Tyr Phe Ala
1               5                   10                  15

(2) INFORMATION FOR SEQ ID NO: 29:

(i) SEQUENCE CHARACTERISTICS:
            (A) LENGTH: 17 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Binding-site
            (B) LOCATION: 9..16

(xi) SEQUENCE DESCRIPTION: SEQ ID NO: 29:

Tyr Lys Asn Asp Val Lys Asn Arg Ser Val Tyr Ile Lys Gly Phe
1               5                   10                  15

Pro Thr
```

-continued

```
(2) INFORMATION FOR SEQ ID NO: 30:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Binding-site
        (B) LOCATION: 1..8

(xi) SEQUENCE DESCRIPTION: SEQ ID NO: 30:

Thr Asp Phe Asn Val Ile Val Glu Ala
1               5

(2) INFORMATION FOR SEQ ID NO: 31:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Binding-site
        (B) LOCATION: 1..8

(xi) SEQUENCE DESCRIPTION: SEQ ID NO: 31:

Glu Gly Ile Ile Leu Phe Lys Glu Lys Ala Lys
1               5                   10

(2) INFORMATION FOR SEQ ID NO: 32:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Binding-site
        (B) LOCATION: 7..14

(xi) SEQUENCE DESCRIPTION: SEQ ID NO: 32:

Lys Val Gln Phe Gln Gly Lys Lys Thr Lys Phe Ala Ser Asp
1               5                   10

(2) INFORMATION FOR SEQ ID NO: 33:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Binding-site
        (B) LOCATION: 1..8

(xi) SEQUENCE DESCRIPTION: SEQ ID NO: 33:

Arg Glu Asp Leu His Ile Leu Phe
1               5
```

(2) INFORMATION FOR SEQ ID NO: 34:

(i) SEQUENCE CHARACTERISTICS:
       (A) LENGTH: 8 amino acids
       (B) TYPE: amino acid
       (C) STRANDEDNESS: single
       (D) TOPOLOGY: linear (ii) MOLECULE TYPE: peptide (ix) FEATURE:
       (A) NAME/KEY: Binding-site
       (B) LOCATION: 1..8

(xi) SEQUENCE DESCRIPTION: SEQ ID NO: 34:

Cys Leu Leu Lys Phe Ser Gly Asp
1          5

(2) INFORMATION FOR SEQ ID NO: 35:

(i) SEQUENCE CHARACTERISTICS:
       (A) LENGTH: 8 amino acids
       (B) TYPE: amino acid
       (C) STRANDEDNESS: single
       (D) TOPOLOGY: linear (ii) MOLECULE TYPE: peptide (ix) FEATURE:
       (A) NAME/KEY: Binding-site
       (B) LOCATION: 1..8

(xi) SEQUENCE DESCRIPTION: SEQ ID NO: 35:

Thr Gly Pro Val Lys Arg Ala Arg
1          5

(2) INFORMATION FOR SEQ ID NO: 36:

(i) SEQUENCE CHARACTERISTICS:
       (A) LENGTH: 10 amino acids
       (B) TYPE: amino acid
       (C) STRANDEDNESS: single
       (D) TOPOLOGY: linear (ii) MOLECULE TYPE: peptide (ix) FEATURE:
       (A) NAME/KEY: Binding-site
       (B) LOCATION: 3..10

(xi) SEQUENCE DESCRIPTION: SEQ ID NO: 36:

Lys Val Glu Ala Lys Leu Arg Ala Lys Gln
1          5              10

(2) INFORMATION FOR SEQ ID NO: 37:

(i) SEQUENCE CHARACTERISTICS:
       (A) LENGTH: 8 amino acids
       (B) TYPE: amino acid
       (C) STRANDEDNESS: single
       (D) TOPOLOGY: linear (ii) MOLECULE TYPE: peptide (ix) FEATURE:
       (A) NAME/KEY: Binding-site
       (B) LOCATION: 1..8

(xi) SEQUENCE DESCRIPTION: SEQ ID NO: 37:

Met Asn Arg Leu His Arg Phe Leu
1          5

(2) INFORMATION FOR SEQ ID NO: 38:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Binding-site
        (B) LOCATION: 2..9

(xi) SEQUENCE DESCRIPTION: SEQ ID NO: 38:

Leu Cys Phe Gly Ser Glu Gly Gly Thr
1               5

(2) INFORMATION FOR SEQ ID NO: 39:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Binding-site
        (B) LOCATION: 1..8

(xi) SEQUENCE DESCRIPTION: SEQ ID NO: 39:

Ser Glu Gly Gly Thr Tyr Tyr Ile Lys Glu Gln
1               5                   10

(2) INFORMATION FOR SEQ ID NO: 40:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Binding-site
        (B) LOCATION: 3..10

(xi) SEQUENCE DESCRIPTION: SEQ ID NO: 40:

Glu Ile Lys Ser Phe Ser Gln Glu Gly Arg Thr
1               5                   10

(2) INFORMATION FOR SEQ ID NO: 41:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Binding-site
        (B) LOCATION: 2..9

(xi) SEQUENCE DESCRIPTION: SEQ ID NO: 41:

Ser Gln Glu Gly Arg Thr Thr Lys Gln

-continued

```
1               5

(2) INFORMATION FOR SEQ ID NO: 42:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Binding-site
        (B) LOCATION: 1..8

(xi) SEQUENCE DESCRIPTION: SEQ ID NO: 42:

Gly Arg Thr Thr Lys Gln Glu Pro Met
1               5

(2) INFORMATION FOR SEQ ID NO: 43:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Binding-site
        (B) LOCATION: 4..11

(xi) SEQUENCE DESCRIPTION: SEQ ID NO: 43:

Ile Ser Thr Lys Gln Ala Ala Phe Lys Ala Val Ser
1               5                   10

(2) INFORMATION FOR SEQ ID NO: 44:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Binding-site
        (B) LOCATION: 1..8

(xi) SEQUENCE DESCRIPTION: SEQ ID NO: 44:

Ala Phe Lys Ala Val Ser Glu Val Cys
1               5

(2) INFORMATION FOR SEQ ID NO: 45:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Binding-site
        (B) LOCATION: 5..12

(xi) SEQUENCE DESCRIPTION: SEQ ID NO: 45:
```

```
Phe Thr Phe Ile Gln Phe Lys Lys Asp Leu Lys Glu Ser Met Lys
1               5                  10                  15
```

(2) INFORMATION FOR SEQ ID NO: 46:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Binding-site
        (B) LOCATION: 2..10

(xi) SEQUENCE DESCRIPTION: SEQ ID NO: 46:

```
Ser Met Lys Cys Gly Met Trp Gly Arg Ala
1               5                  10
```

(2) INFORMATION FOR SEQ ID NO: 47:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 47:

```
Gly Met Trp Gly Arg Ala Leu Arg Lys Ala Ile Ala
1               5                  10
```

(2) INFORMATION FOR SEQ ID NO: 48:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Binding-site
        (B) LOCATION: 9..16

(xi) SEQUENCE DESCRIPTION: SEQ ID NO: 48:

```
Ala Leu Ala Val Thr Lys Tyr Lys Gln Arg Asn Gly Trp Ser His
1               5                  10                  15
Lys Asp Leu Leu Arg Leu Ser His
                20
```

(2) INFORMATION FOR SEQ ID NO: 49:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Binding-site
        (B) LOCATION: 3..10

(xi) SEQUENCE DESCRIPTION: SEQ ID NO: 49:

```
Leu Leu Arg Leu Ser His Leu Lys Pro Ser Ser
1               5                   10
```

(2) INFORMATION FOR SEQ ID NO: 50:

(i) SEQUENCE CHARACTERISTICS:
      (A) LENGTH: 8 amino acids
      (B) TYPE: amino acid
      (C) STRANDEDNESS: single
      (D) TOPOLOGY: linear (ii) MOLECULE TYPE: peptide (ix) FEATURE:
      (A) NAME/KEY: Binding-site
      (B) LOCATION: 1..8

(xi) SEQUENCE DESCRIPTION: SEQ ID NO: 50:

```
His Glu Leu Tyr Lys Glu Lys Ala
1               5
```

(2) INFORMATION FOR SEQ ID NO: 51:

(i) SEQUENCE CHARACTERISTICS:
      (A) LENGTH: 9 amino acids
      (B) TYPE: amino acid
      (C) STRANDEDNESS: single
      (D) TOPOLOGY: linear (ii) MOLECULE TYPE: peptide (ix) FEATURE:
      (A) NAME/KEY: Binding-site
      (B) LOCATION: 1..8

(xi) SEQUENCE DESCRIPTION: SEQ ID NO: 51:

```
Leu Tyr Lys Glu Lys Ala Leu Ser Val
1               5
```

(2) INFORMATION FOR SEQ ID NO: 52:

(i) SEQUENCE CHARACTERISTICS:
      (A) LENGTH: 14 amino acids
      (B) TYPE: amino acid
      (C) STRANDEDNESS: single
      (D) TOPOLOGY: linear (ii) MOLECULE TYPE: peptide (ix) FEATURE:
      (A) NAME/KEY: Binding-site
      (B) LOCATION: 7..14

(xi) SEQUENCE DESCRIPTION: SEQ ID NO: 52:

```
Lys Ala Leu Ser Val Glu Thr Glu Lys Leu Leu Lys Tyr Leu
1               5                   10
```

(2) INFORMATION FOR SEQ ID NO: 53:

(i) SEQUENCE CHARACTERISTICS:
      (A) LENGTH: 8 amino acids
      (B) TYPE: amino acid
      (C) STRANDEDNESS: single
      (D) TOPOLOGY: linear (ii) MOLECULE TYPE: peptide (ix) FEATURE:
      (A) NAME/KEY: Binding-site
      (B) LOCATION: 1..8

(xi) SEQUENCE DESCRIPTION: SEQ ID NO: 53:

```
Lys Leu Leu Lys Tyr Leu Glu Ala
1               5

(2) INFORMATION FOR SEQ ID NO: 54:

(i) SEQUENCE CHARACTERISTICS:
         (A) LENGTH: 13 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Binding-site
         (B) LOCATION: 6..13

(xi) SEQUENCE DESCRIPTION: SEQ ID NO: 54:

Leu Glu Ala Val Glu Lys Val Lys Arg Thr Lys Asp Glu
1               5                   10

(2) INFORMATION FOR SEQ ID NO: 55:

(i) SEQUENCE CHARACTERISTICS:
         (A) LENGTH: 22 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Binding-site
         (B) LOCATION: 1..14

(xi) SEQUENCE DESCRIPTION: SEQ ID NO: 55:

His Leu Leu Thr Asn His Leu Lys Ser Lys Glu Val Trp Lys Ala
1               5                   10                  15
Leu Leu Gln Glu Met Pro Leu
                20

(2) INFORMATION FOR SEQ ID NO: 56:

(i) SEQUENCE CHARACTERISTICS:
         (A) LENGTH: 11 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Binding-site
         (B) LOCATION: 1..8

(xi) SEQUENCE DESCRIPTION: SEQ ID NO: 56:

Ala Leu Leu Arg Asn Leu Gly Lys Met Thr Ala
1               5                   10

(2) INFORMATION FOR SEQ ID NO: 57:

(i) SEQUENCE CHARACTERISTICS:
         (A) LENGTH: 8 amino acids
         (B) TYPE: amino acid
         (C) STRANDEDNESS: single
         (D) TOPOLOGY: linear (ii) MOLECULE TYPE: peptide (ix) FEATURE:
```

(A) NAME/KEY: Binding-site
                (B) LOCATION: 1..8

(xi) SEQUENCE DESCRIPTION: SEQ ID NO: 57:

Leu Gly Lys Met Thr Ala Asn Ser
1               5

(2) INFORMATION FOR SEQ ID NO: 58:

(i) SEQUENCE CHARACTERISTICS:
                (A) LENGTH: 17 amino acids
                (B) TYPE: amino acid
                (C) STRANDEDNESS: single
                (D) TOPOLOGY: linear (ii) MOLECULE TYPE: peptide (ix) FEATURE:
                (A) NAME/KEY: Binding-site
                (B) LOCATION: 6..15

(xi) SEQUENCE DESCRIPTION: SEQ ID NO: 58:

Leu Cys Asn Glu Lys Leu Leu Lys Lys Ala Arg Ile His Pro Phe
1               5                   10                  15

His Ile (2) INFORMATION FOR SEQ ID NO: 59:

(i) SEQUENCE CHARACTERISTICS:
                (A) LENGTH: 18 amino acids
                (B) TYPE: amino acid
                (C) STRANDEDNESS: single
                (D) TOPOLOGY: linear (ii) MOLECULE TYPE: peptide (ix) FEATURE:
                (A) NAME/KEY: Binding-site
                (B) LOCATION: 2..9

(xi) SEQUENCE DESCRIPTION: SEQ ID NO: 59:

Thr Tyr Lys Thr Gly His Gly Leu Arg Gly Lys Leu Lys Trp Arg
1               5                   10                  15

Pro Asp Glu (2) INFORMATION FOR SEQ ID NO: 60:

(i) SEQUENCE CHARACTERISTICS:
                (A) LENGTH: 8 amino acids
                (B) TYPE: amino acid
                (C) STRANDEDNESS: single
                (D) TOPOLOGY: linear (ii) MOLECULE TYPE: peptide (ix) FEATURE:
                (A) NAME/KEY: Binding-site
                (B) LOCATION: 1..8

(xi) SEQUENCE DESCRIPTION: SEQ ID NO: 60:

Ala Leu Asp Ala Ala Phe Tyr Lys
1               5

(2) INFORMATION FOR SEQ ID NO: 61:

(i) SEQUENCE CHARACTERISTICS:
                (A) LENGTH: 20 amino acids
                (B) TYPE: amino acid
                (C) STRANDEDNESS: single (D) TOPOLOGY: linear (ii) MOLECULE TYPE: peptide (ix) FEATURE:
         (A) NAME/KEY: Binding-site
         (B) LOCATION: 1..8

(xi) SEQUENCE DESCRIPTION: SEQ ID NO: 61:

Ala Ala Phe Tyr Lys Thr Phe Lys Thr Val Glu Pro Thr Gly Lys
1               5                  10                  15

Arg Phe Leu Leu Ala
            20

(2) INFORMATION FOR SEQ ID NO: 62:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (ix) FEATURE:
         (A) NAME/KEY: Binding-site
         (B) LOCATION: 1..8

(xi) SEQUENCE DESCRIPTION: SEQ ID NO: 62:

Ala Ser Met Asn Gln Arg Val Leu Gly Ser
1               5                  10

(2) INFORMATION FOR SEQ ID NO: 63:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
         (A) NAME/KEY: Binding-site
         (B) LOCATION: 1..8

(xi) SEQUENCE DESCRIPTION: SEQ ID NO: 63:

Ala Met Cys Met Val Val Thr Arg
1               5

(2) INFORMATION FOR SEQ ID NO: 64:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
         (A) NAME/KEY: Binding-site
         (B) LOCATION: 1..8

(xi) SEQUENCE DESCRIPTION: SEQ ID NO: 64:

Ala Phe Ser Asp Glu Met Val Pro
1               5

(2) INFORMATION FOR SEQ ID NO: 65:

```
    (i) SEQUENCE CHARACTERISTICS:
         (A) LENGTH: 8 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Binding-site
         (B) LOCATION: 1..8

(xi) SEQUENCE DESCRIPTION: SEQ ID NO: 65:

Val Pro Cys Pro Val Thr Thr Asp
1               5

(2) INFORMATION FOR SEQ ID NO: 66:

(i) SEQUENCE CHARACTERISTICS:
         (A) LENGTH: 8 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Binding-site
         (B) LOCATION: 1..8

(xi) SEQUENCE DESCRIPTION: SEQ ID NO: 66:

Val Leu Met Ala Met Ser Gln Ile
1               5

(2) INFORMATION FOR SEQ ID NO: 67:

(i) SEQUENCE CHARACTERISTICS:
         (A) LENGTH: 8 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Binding-site
         (B) LOCATION: 1..8

(xi) SEQUENCE DESCRIPTION: SEQ ID NO: 67:

Thr Asp Cys Ser Leu Pro Met Ile
1               5

(2) INFORMATION FOR SEQ ID NO: 68:

(i) SEQUENCE CHARACTERISTICS:
         (A) LENGTH: 15 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Binding-site
         (B) LOCATION: 3..10

(xi) SEQUENCE DESCRIPTION: SEQ ID NO: 68:

Cys Ser Leu Pro Met Ile Trp Ala Gln Lys Thr Asn Thr Pro Ala
1               5                  10                  15

(2) INFORMATION FOR SEQ ID NO: 69:
```

```
    (i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Binding-site
        (B) LOCATION: 1..8

(xi) SEQUENCE DESCRIPTION: SEQ ID NO: 69:

Thr Phe Ala Gly Gly Val His Pro Ala Ile
1               5                   10

(2) INFORMATION FOR SEQ ID NO: 70:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Binding-site
        (B) LOCATION: 4..11

(xi) SEQUENCE DESCRIPTION: SEQ ID NO: 70:

Ile Ala Leu Arg Glu Tyr Arg Lys Lys Met Asp Ile Pro Ala Lys
1               5                   10                  15

Leu (2) INFORMATION FOR SEQ ID NO: 71:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 71:

Ile Val Thr Lys Tyr Ile Thr Lys Gly Trp Lys Glu Val His Glu Leu
1               5                   10                  15

(2) INFORMATION FOR SEQ ID NO: 72:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Binding-site
        (B) LOCATION: 1..8

(xi) SEQUENCE DESCRIPTION: SEQ ID NO: 72:

Ala Leu Phe Ala Pro Arg Asp Pro
1               5

(2) INFORMATION FOR SEQ ID NO: 73:
```

```
    (i) SEQUENCE CHARACTERISTICS:
         (A) LENGTH: 10 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Binding-site
         (B) LOCATION: 1..8

(xi) SEQUENCE DESCRIPTION: SEQ ID NO: 73:

Glu Arg Met Glu Arg Lys Arg Arg Glu Lys
1               5                   10

(2) INFORMATION FOR SEQ ID NO: 74:

(i) SEQUENCE CHARACTERISTICS:
         (A) LENGTH: 14 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Binding-site
         (B) LOCATION: 2..9

(xi) SEQUENCE DESCRIPTION: SEQ ID NO: 74:

His Met Val Tyr Ser Lys Arg Ser Gly Lys Pro Arg Gly Tyr
1               5                   10

(2) INFORMATION FOR SEQ ID NO: 75:

(i) SEQUENCE CHARACTERISTICS:
         (A) LENGTH: 15 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Binding-site
         (B) LOCATION: 6..13

(xi) SEQUENCE DESCRIPTION: SEQ ID NO: 75:

Tyr Lys His Ala Asp Gly Lys Lys Ile Asp Gly Arg Arg Val Leu
1               5                   10                  15

(2) INFORMATION FOR SEQ ID NO: 76:

(i) SEQUENCE CHARACTERISTICS:
         (A) LENGTH: 8 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Binding-site
         (B) LOCATION: 1..8

(xi) SEQUENCE DESCRIPTION: SEQ ID NO: 76:

Val Glu Arg Gly Arg Thr Val Lys
1               5

(2) INFORMATION FOR SEQ ID NO: 77:
```

```
    (i) SEQUENCE CHARACTERISTICS:
         (A) LENGTH: 8 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Binding-site
         (B) LOCATION: 1..8

(xi) SEQUENCE DESCRIPTION: SEQ ID NO: 77:

Val Lys Gly Trp Arg Pro Arg Arg
1               5

(2) INFORMATION FOR SEQ ID NO: 78:

(i) SEQUENCE CHARACTERISTICS:
         (A) LENGTH: 8 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Binding-site
         (B) LOCATION: 1..8

(xi) SEQUENCE DESCRIPTION: SEQ ID NO: 78:

Arg Arg Ser Arg Ser Arg Asp Lys
1               5

(2) INFORMATION FOR SEQ ID NO: 79:

(i) SEQUENCE CHARACTERISTICS:
         (A) LENGTH: 8 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Binding-site
         (B) LOCATION: 1..8

(xi) SEQUENCE DESCRIPTION: SEQ ID NO: 79:

Arg Arg Arg Ser Arg Glu Arg Ser
1               5

(2) INFORMATION FOR SEQ ID NO: 80:

(i) SEQUENCE CHARACTERISTICS:
         (A) LENGTH: 8 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Binding-site
         (B) LOCATION: 1..8

(xi) SEQUENCE DESCRIPTION: SEQ ID NO: 80:

Ser Arg Glu Arg Ser Lys Asp Lys
1               5
```

```
(2) INFORMATION FOR SEQ ID NO: 81:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Binding-site
        (B) LOCATION: 8..15

(xi) SEQUENCE DESCRIPTION: SEQ ID NO: 81:

Lys Asp Lys Asp Arg Asp Arg Lys Arg Arg Ser Ser Arg Ser Arg
1               5                   10                  15

(2) INFORMATION FOR SEQ ID NO: 82:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Binding-site
        (B) LOCATION: 1..8

(xi) SEQUENCE DESCRIPTION: SEQ ID NO: 82:

Arg Arg Ser His Arg Ser Glu Arg
1               5

(2) INFORMATION FOR SEQ ID NO: 83:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Binding-site
        (B) LOCATION: 2..9

(xi) SEQUENCE DESCRIPTION: SEQ ID NO: 83:

Asn Leu Asn Glu Lys Ile Lys Lys Asp
1               5

(2) INFORMATION FOR SEQ ID NO: 84:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Binding-site
        (B) LOCATION: 2..9

(xi) SEQUENCE DESCRIPTION: SEQ ID NO: 84:

Ile Lys Lys Asp Glu Leu Lys Lys Ser Leu
1               5                   10
```

```
(2) INFORMATION FOR SEQ ID NO: 85:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Binding-site
        (B) LOCATION: 3..10

(xi) SEQUENCE DESCRIPTION: SEQ ID NO: 85:

Leu Val Ser Arg Ser Leu Lys Met Arg Gly Gln Ala Phe
1               5                   10

(2) INFORMATION FOR SEQ ID NO: 86:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Binding-site
        (B) LOCATION: 4..11

(xi) SEQUENCE DESCRIPTION: SEQ ID NO: 86:

Gln Gly Phe Pro Phe Tyr Asp Lys Pro Met Arg Ile
1               5                   10

(2) INFORMATION FOR SEQ ID NO: 87:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Binding-site
        (B) LOCATION: 1..8

(xi) SEQUENCE DESCRIPTION: SEQ ID NO: 87:

Ile Ile Ala Lys Met Lys Gly Thr Phe
1               5

(2) INFORMATION FOR SEQ ID NO: 88:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Binding-site
        (B) LOCATION: 3..10

(xi) SEQUENCE DESCRIPTION: SEQ ID NO: 88:

Glu Arg Asp Arg Lys Arg Glu Lys Arg Lys Pro Lys Ser
1               5                   10
```

(2) INFORMATION FOR SEQ ID NO: 89:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Binding-site
        (B) LOCATION: 1..8

(xi) SEQUENCE DESCRIPTION: SEQ ID NO: 89:

Gln Glu Thr Pro Ala Thr Lys Lys Ala
1               5

(2) INFORMATION FOR SEQ ID NO: 90:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 90:

Ala Leu Gln Gly Phe Lys Ile Thr
1               5

(2) INFORMATION FOR SEQ ID NO: 91:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Binding-site
        (B) LOCATION: 2..9

(xi) SEQUENCE DESCRIPTION: SEQ ID NO: 91:

Ala Met Lys Ile Ser Phe Ala Lys Lys
1               5

(2) INFORMATION FOR SEQ ID NO: 92:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Binding-site
        (B) LOCATION: 10..17

(xi) SEQUENCE DESCRIPTION: SEQ ID NO: 92:

Ser Val Arg Lys Thr His Cys Ser Gly Arg Lys His Lys Glu Asn
1               5                   10                  15
Val Lys Asp (2) INFORMATION FOR SEQ ID NO: 93:

(i) SEQUENCE CHARACTERISTICS:
       (A) LENGTH: 8 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO: 93:

Lys Asp Tyr Tyr Gln Lys Trp Met
1               5

(2) INFORMATION FOR SEQ ID NO: 94:

(i) SEQUENCE CHARACTERISTICS:
       (A) LENGTH: 9 amino acids
       (B) TYPE: amino acid
       (C) STRANDEDNESS: single
       (D) TOPOLOGY: linear (ii) MOLECULE TYPE: peptide (ix) FEATURE:
       (A) NAME/KEY: Binding-site
       (B) LOCATION: 1..8

(xi) SEQUENCE DESCRIPTION: SEQ ID NO: 94:

Ala Phe Gln Gln Gly Lys Ile Pro Pro
1               5

(2) INFORMATION FOR SEQ ID NO: 95:

(i) SEQUENCE CHARACTERISTICS:
       (A) LENGTH: 8 amino acids
       (B) TYPE: amino acid
       (C) STRANDEDNESS: single
       (D) TOPOLOGY: linear (ii) MOLECULE TYPE: peptide (ix) FEATURE:
       (A) NAME/KEY: Binding-site
       (B) LOCATION: 1..8

(xi) SEQUENCE DESCRIPTION: SEQ ID NO: 95:

Lys Ile Pro Pro Thr Pro Phe Ser
1               5

(2) INFORMATION FOR SEQ ID NO: 96:

(i) SEQUENCE CHARACTERISTICS:
       (A) LENGTH: 8 amino acids
       (B) TYPE: amino acid
       (C) STRANDEDNESS: single
       (D) TOPOLOGY: linear (ii) MOLECULE TYPE: peptide (ix) FEATURE:
       (A) NAME/KEY: Binding-site
       (B) LOCATION: 1..8

(xi) SEQUENCE DESCRIPTION: SEQ ID NO: 96:

Pro Pro Pro Pro Ser Leu Pro Gly
1               5

(2) INFORMATION FOR SEQ ID NO: 97:

```
    (i) SEQUENCE CHARACTERISTICS:
         (A) LENGTH: 8 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Binding-site
         (B) LOCATION: 1..8

(xi) SEQUENCE DESCRIPTION: SEQ ID NO: 97:

Ser Leu Pro Gly Pro Pro Arg Pro
1               5

(2) INFORMATION FOR SEQ ID NO: 98:

(i) SEQUENCE CHARACTERISTICS:
         (A) LENGTH: 10 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Binding-site
         (B) LOCATION: 2..9

(xi) SEQUENCE DESCRIPTION: SEQ ID NO: 98:

Gly Pro Pro Arg Pro Gly Met Met Pro Ala
1               5                   10

(2) INFORMATION FOR SEQ ID NO: 99:

(i) SEQUENCE CHARACTERISTICS:
         (A) LENGTH: 8 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Binding-site
         (B) LOCATION: 1..8

(xi) SEQUENCE DESCRIPTION: SEQ ID NO: 99:

Pro Pro Pro Pro Gly Met Met Pro
1               5

(2) INFORMATION FOR SEQ ID NO: 100:

(i) SEQUENCE CHARACTERISTICS:
         (A) LENGTH: 9 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Binding-site
         (B) LOCATION: 1..8

(xi) SEQUENCE DESCRIPTION: SEQ ID NO: 100:

Gly Pro Ala Pro Gly Met Arg Pro Pro
1               5

(2) INFORMATION FOR SEQ ID NO: 101:
```

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Binding-site
        (B) LOCATION: 1..8

(xi) SEQUENCE DESCRIPTION: SEQ ID NO: 101:

Pro Pro Met Met Arg Pro Pro Ala
1               5

(2) INFORMATION FOR SEQ ID NO: 102:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Binding-site
        (B) LOCATION: 1..8

(xi) SEQUENCE DESCRIPTION: SEQ ID NO: 102:

Pro Gly Met Thr Arg Pro Asp Arg
1               5

(2) INFORMATION FOR SEQ ID NO: 103:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 103:

Lys Trp Ile Asp Phe Val Arg Gly Ala Lys
1               5                   10

(2) INFORMATION FOR SEQ ID NO: 104:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 104:

Ile Asp Phe Val Arg Gly Ala Lys
1               5

(2) INFORMATION FOR SEQ ID NO: 105:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 105:

Lys Ser Lys Gly Arg Arg Phe Lys
1               5

(2) INFORMATION FOR SEQ ID NO: 106:

(i) SEQUENCE CHARACTERISTICS:
                (A) LENGTH: 8 amino acids
                (B) TYPE: amino acid
                (C) STRANDEDNESS: single
                (D) TOPOLOGY: linear (ii) MOLECULE TYPE: peptide (xi) SEQUENCE DESCRIPTION: SEQ ID NO: 106:

Leu Arg Asn Lys Glu Val Thr Trp
1               5

(2) INFORMATION FOR SEQ ID NO: 107:

(i) SEQUENCE CHARACTERISTICS:
                (A) LENGTH: 8 amino acids
                (B) TYPE: amino acid
                (C) STRANDEDNESS: single
                (D) TOPOLOGY: linear (ii) MOLECULE TYPE: peptide (xi) SEQUENCE DESCRIPTION: SEQ ID NO: 107:

Phe Val Val Phe Asp Ser Ile Glu
1               5

(2) INFORMATION FOR SEQ ID NO: 108:

(i) SEQUENCE CHARACTERISTICS:
                (A) LENGTH: 8 amino acids
                (B) TYPE: amino acid
                (C) STRANDEDNESS: single
                (D) TOPOLOGY: linear (ii) MOLECULE TYPE: peptide (xi) SEQUENCE DESCRIPTION: SEQ ID NO: 108:

Ile Leu Phe Lys Asp Asp Tyr Phe
1               5

(2) INFORMATION FOR SEQ ID NO: 109:

(i) SEQUENCE CHARACTERISTICS:
                (A) LENGTH: 8 amino acids
                (B) TYPE: amino acid
                (C) STRANDEDNESS: single
                (D) TOPOLOGY: linear (ii) MOLECULE TYPE: peptide (xi) SEQUENCE DESCRIPTION: SEQ ID NO: 109:

Ser Val Tyr Ile Lys Gly Phe Pro
1               5

(2) INFORMATION FOR SEQ ID NO: 110:

(i) SEQUENCE CHARACTERISTICS:
                (A) LENGTH: 8 amino acids
                (B) TYPE: amino acid
                (C) STRANDEDNESS: single
                (D) TOPOLOGY: linear (ii) MOLECULE TYPE: peptide (xi) SEQUENCE DESCRIPTION: SEQ ID NO: 110:

Thr Asp Phe Asn Val Ile Val Glu
1               5

(2) INFORMATION FOR SEQ ID NO: 111:

(i) SEQUENCE CHARACTERISTICS:
              (A) LENGTH: 8 amino acids
              (B) TYPE: amino acid
              (C) STRANDEDNESS: single
              (D) TOPOLOGY: linear (ii) MOLECULE TYPE: peptide (xi) SEQUENCE DESCRIPTION: SEQ ID NO: 111:

Asp Phe Asn Val Ile Val Glu Ala
1               5

(2) INFORMATION FOR SEQ ID NO: 112:

(i) SEQUENCE CHARACTERISTICS:
              (A) LENGTH: 8 amino acids
              (B) TYPE: amino acid
              (C) STRANDEDNESS: single
              (D) TOPOLOGY: linear (ii) MOLECULE TYPE: peptide (xi) SEQUENCE DESCRIPTION: SEQ ID NO: 112:

Glu Gly Ile Ile Leu Phe Lys Glu
1               5

(2) INFORMATION FOR SEQ ID NO: 113:

(i) SEQUENCE CHARACTERISTICS:
              (A) LENGTH: 8 amino acids
              (B) TYPE: amino acid
              (C) STRANDEDNESS: single
              (D) TOPOLOGY: linear (ii) MOLECULE TYPE: peptide (xi) SEQUENCE DESCRIPTION: SEQ ID NO: 113:

Lys Lys Thr Lys Phe Ala Ser Asp
1               5

(2) INFORMATION FOR SEQ ID NO: 114:

(i) SEQUENCE CHARACTERISTICS:
              (A) LENGTH: 8 amino acids
              (B) TYPE: amino acid
              (C) STRANDEDNESS: single
              (D) TOPOLOGY: linear (ii) MOLECULE TYPE: peptide (xi) SEQUENCE DESCRIPTION: SEQ ID NO: 114:

Glu Ala Lys Leu Arg Ala Lys Gln
1               5

(2) INFORMATION FOR SEQ ID NO: 115:

(i) SEQUENCE CHARACTERISTICS:
              (A) LENGTH: 8 amino acids
              (B) TYPE: amino acid
              (C) STRANDEDNESS: single (D) TOPOLOGY: linear (ii) MOLECULE TYPE: peptide (xi) SEQUENCE DESCRIPTION: SEQ ID NO: 115:

Cys Phe Gly Ser Glu Gly Gly Thr
1               5

(2) INFORMATION FOR SEQ ID NO: 116:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 116:

Pro Ala Pro Gly Met Arg Pro Pro
1               5

(2) INFORMATION FOR SEQ ID NO: 117:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 117:

Pro Pro Pro Gly Met Ile Pro Pro
1               5

(2) INFORMATION FOR SEQ ID NO: 118:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 118:

Asn Arg Leu Asn Arg Leu Thr Thr
1               5

(2) INFORMATION FOR SEQ ID NO: 119:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 5
        (D) OTHER INFORMATION: /note= "Xaa is an undetermined amino
            acid"

(xi) SEQUENCE DESCRIPTION: SEQ ID NO: 119:

Pro Pro Pro Gly Xaa Arg
1               5

(2) INFORMATION FOR SEQ ID NO: 120:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 120:

Pro Pro Pro Pro Pro
1               5

(2) INFORMATION FOR SEQ ID NO: 121:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 121:

Pro Gly Ile Arg Gly Pro Pro Pro
1               5

(2) INFORMATION FOR SEQ ID NO: 122:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 122:

Pro Pro Pro Gly Ile Arg Pro Pro
1               5

(2) INFORMATION FOR SEQ ID NO: 123:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Misc Feature
        (B) LOCATION: 6
        (D) OTHER INFORMATION: /note= "The Xaa at position 6 can be
            R, F, G, H, I, K, S, T, V,
            and Y."

(xi) SEQUENCE DESCRIPTION: SEQ ID NO: 123:

Pro Pro Pro Gly Met Xaa Pro Pro
1               5

(2) INFORMATION FOR SEQ ID NO: 124:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 124:

Pro Pro Pro Gly Met Arg Pro
1               5

(2) INFORMATION FOR SEQ ID NO: 125:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 125:

Pro Pro Pro Gly Met Arg
1               5

(2) INFORMATION FOR SEQ ID NO: 126:
            former #219
    (i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 126:

Trp Ala Gln Lys Thr Asn Thr Pro
1               5

(2) INFORMATION FOR SEQ ID NO: 127:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 127:

Pro Pro Pro Gly Ile Arg Gly Pro
1               5

(2) INFORMATION FOR SEQ ID NO: 128:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 128:

Pro Gln Gly Arg
1

(2) INFORMATION FOR SEQ ID NO: 129:

(i) SEQUENCE CHARACTERISTICS:
        (A) LENGTH: 5 amino acids
        (B) TYPE: amino acid
        (C) STRANDEDNESS: single

```
            (D) TOPOLOGY: linear (ii) MOLECULE TYPE: peptide (xi) SEQUENCE DESCRIPTION: SEQ ID NO: 129:

Pro Pro Pro Gly Met
1               5

(2) INFORMATION FOR SEQ ID NO: 130:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 130:

Pro Pro Pro Gly
1

(2) INFORMATION FOR SEQ ID NO: 131:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 131:

Pro Pro Gly Met
1

(2) INFORMATION FOR SEQ ID NO: 132:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 132:

Pro Gly Met Arg
1

(2) INFORMATION FOR SEQ ID NO: 133:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 133:

Gly Met Arg Pro
1

(2) INFORMATION FOR SEQ ID NO: 134:

(i) SEQUENCE CHARACTERISTICS:
            (A) LENGTH: 4 amino acids
            (B) TYPE: amino acid
```

```
        (C) STRANDEDNESS: single
        (D) TOPOLOGY: linear (ii) MOLECULE TYPE: peptide (xi) SEQUENCE DESCRIPTION: SEQ ID NO: 134:

Pro Pro Pro Pro
1

(2) INFORMATION FOR SEQ ID NO: 135:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 135:

Pro Pro Pro Pro
1

(2) INFORMATION FOR SEQ ID NO: 136:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 136:

Asn Ile Gln Met Arg Arg Thr Leu His Lys Ala Phe Lys
1               5                   10

(2) INFORMATION FOR SEQ ID NO: 137:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 137:

Arg Thr Leu His Lys Ala Phe Lys
1               5

(2) INFORMATION FOR SEQ ID NO: 138:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 138:

Tyr Phe Gly Asp Phe Asn Leu Pro
1               5

(2) INFORMATION FOR SEQ ID NO: 139:

(i) SEQUENCE CHARACTERISTICS:
        (A) LENGTH: 8 amino acids
```

(B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 139:

Val Pro Leu Glu Ile Met Ile Lys
1               5

(2) INFORMATION FOR SEQ ID NO: 140:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 140:

Lys Ile Arg Arg Ser Pro Ser Lys
1               5

(2) INFORMATION FOR SEQ ID NO: 141:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 141:

Glu Gly Gly Thr Tyr Tyr Ile Lys Glu Gln
1               5                   10

(2) INFORMATION FOR SEQ ID NO: 142:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 142:

Gly Thr Tyr Tyr Ile Lys Glu Gln
1               5

(2) INFORMATION FOR SEQ ID NO: 143:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 143:

Gly Thr Tyr Tyr Ile
1               5

(2) INFORMATION FOR SEQ ID NO: 144:

(i) SEQUENCE CHARACTERISTICS:

(A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 144:

Lys Ser Phe Ser Gln Glu Gly Arg
1               5

(2) INFORMATION FOR SEQ ID NO: 145:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 145:

Ser Thr Lys Gln Ala Ala Phe Lys Ala Val
1               5                   10

(2) INFORMATION FOR SEQ ID NO: 146:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 146:

Lys Gln Ala Ala Phe Lys Ala Val
1               5

(2) INFORMATION FOR SEQ ID NO: 147:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 147:

Gln Phe Lys Lys Asp Leu Lys Glu
1               5

(2) INFORMATION FOR SEQ ID NO: 148:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 148:

Met Lys Cys Gly Met Trp Gly Arg Ala
1               5

(2) INFORMATION FOR SEQ ID NO: 149:

```
    (i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 149:

Gly Arg Ala Leu Arg Lys Ala Ile
1               5

(2) INFORMATION FOR SEQ ID NO: 150:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 150:

Thr Lys Tyr Lys Gln Arg Asn Gly
1               5

(2) INFORMATION FOR SEQ ID NO: 151:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 151:

Gln Arg Asn Gly Trp Ser His Lys
1               5

(2) INFORMATION FOR SEQ ID NO: 152:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 152:

Arg Leu Ser His Leu Lys Pro Ser
1               5

(2) INFORMATION FOR SEQ ID NO: 153:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 153:

Thr Lys Tyr Ile Thr Lys Gly Trp
1               5

(2) INFORMATION FOR SEQ ID NO: 154:
```

(i) SEQUENCE CHARACTERISTICS:
    (A) LENGTH: 8 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO: 154:

Ile Thr Lys Gly Trp Lys Glu Val
1               5

(2) INFORMATION FOR SEQ ID NO: 155:

(i) SEQUENCE CHARACTERISTICS:
    (A) LENGTH: 8 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO: 155:

Thr Glu Lys Leu Leu Lys Tyr Leu
1               5

(2) INFORMATION FOR SEQ ID NO: 156:

(i) SEQUENCE CHARACTERISTICS:
    (A) LENGTH: 8 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO: 156:

Lys Val Lys Arg Thr Lys Asp Glu
1               5

(2) INFORMATION FOR SEQ ID NO: 157:

(i) SEQUENCE CHARACTERISTICS:
    (A) LENGTH: 8 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO: 157:

Leu Lys Ser Lys Glu Val Trp Lys
1               5

(2) INFORMATION FOR SEQ ID NO: 158:

(i) SEQUENCE CHARACTERISTICS:
    (A) LENGTH: 8 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO: 158:

Lys Ser Lys Glu Val Trp Lys Ala
1               5

```
(2) INFORMATION FOR SEQ ID NO: 159:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 159:

Ser Lys Glu Val Trp Lys
1               5

(2) INFORMATION FOR SEQ ID NO: 160:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 160:

Arg Asn Leu Gly Lys Met Thr
1               5

(2) INFORMATION FOR SEQ ID NO: 161:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 161:

Leu Leu Lys Lys Ala Arg Ile
1               5

(2) INFORMATION FOR SEQ ID NO: 162:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 162:

Lys Lys Ala Arg Ile His Pro Phe
1               5

(2) INFORMATION FOR SEQ ID NO: 163:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 163:

Tyr Lys Thr Gly His Gly Leu
1               5
```

(2) INFORMATION FOR SEQ ID NO: 164:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 164:

Glu Pro Thr Gly Lys Arg Phe Leu
1               5

(2) INFORMATION FOR SEQ ID NO: 165:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 165:

Leu Pro Met Ile Trp Ala Gln Lys Thr Asn Thr Pro Ala
1               5                  10

(2) INFORMATION FOR SEQ ID NO: 166:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 166:

Thr Phe Ala Gly Gly Val His Pro
1               5

(2) INFORMATION FOR SEQ ID NO: 167:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 167:

Arg Glu Tyr Arg Lys Lys Met Asp
1               5

(2) INFORMATION FOR SEQ ID NO: 168:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 168:

Ile Gly Thr Phe Lys Ala Phe Asp
1               5

-continued (2) INFORMATION FOR SEQ ID NO: 169:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 169:

Thr Phe Lys Ala Phe Asp Lys His
1               5

(2) INFORMATION FOR SEQ ID NO: 170:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 170:

Asp Cys Asp Glu Phe Arg Lys Ile
1               5

(2) INFORMATION FOR SEQ ID NO: 171:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 171:

Cys Asp Glu Phe Ala Lys Ile Lys
1               5

(2) INFORMATION FOR SEQ ID NO: 172:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 172:

Asp Glu Phe Arg Lys Ile Lys Pro
1               5

(2) INFORMATION FOR SEQ ID NO: 173:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 173:

Glu Phe Arg Lys Ile Lys Pro Lys (2) INFORMATION FOR SEQ ID NO: 174:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 174:

Phe Arg Lys Ile Lys Pro Lys Asn
1         5

(2) INFORMATION FOR SEQ ID NO: 175:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 175:

Arg Lys Ile Lys Pro Lys Asn Ala
1         5

(2) INFORMATION FOR SEQ ID NO: 176:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 176:

Lys Ile Lys Pro Lys Asn Ala Lys
1         5

(2) INFORMATION FOR SEQ ID NO: 177:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 177:

Ile Lys Pro Lys Asn Ala Lys Gln
1         5

(2) INFORMATION FOR SEQ ID NO: 178:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 178:

```
Lys Pro Lys Asn Ala Lys Gln Pro
1               5

(2) INFORMATION FOR SEQ ID NO: 179:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 179:

Pro Lys Asn Ala Lys Gln Pro Glu
1               5

(2) INFORMATION FOR SEQ ID NO: 180:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 180:

Pro Gly Val Gly Arg Ala Ala Gly
1               5

(2) INFORMATION FOR SEQ ID NO: 181:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 181:

Val Arg Gly Val Gly Gly Pro Ser
1               5

(2) INFORMATION FOR SEQ ID NO: 182:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 182:

Gln Gln Val Met Thr Pro Gln Gly
1               5

(2) INFORMATION FOR SEQ ID NO: 183:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 183:
```

```
Gln Val Met Thr Pro Gln Gly Arg
1               5
```

(2) INFORMATION FOR SEQ ID NO: 184:

(i) SEQUENCE CHARACTERISTICS:
       (A) LENGTH: 8 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO: 184:

```
Val Met Thr Pro Gln Gly Arg Gly
1               5
```

(2) INFORMATION FOR SEQ ID NO: 185:

(i) SEQUENCE CHARACTERISTICS:
       (A) LENGTH: 8 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO: 185:

```
Met Thr Pro Gln Gly Asx Gly Thr
1               5
```

(2) INFORMATION FOR SEQ ID NO: 186:

(i) SEQUENCE CHARACTERISTICS:
       (A) LENGTH: 8 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO: 186:

```
Thr Pro Gln Gly Arg Gly Thr Val
1               5
```

(2) INFORMATION FOR SEQ ID NO: 187:

(i) SEQUENCE CHARACTERISTICS:
       (A) LENGTH: 8 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO: 187:

```
Pro Gln Gly Arg Gly Thr Val Ala
1               5
```

(2) INFORMATION FOR SEQ ID NO: 188:

(i) SEQUENCE CHARACTERISTICS:
       (A) LENGTH: 8 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO: 188:

Gln Gly Arg Gly Thr Val Ala Ala
1               5

(2) INFORMATION FOR SEQ ID NO: 189:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 189:

Ala Pro Thr Gln Tyr Pro Pro Gly
1               5

(2) INFORMATION FOR SEQ ID NO: 190:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 190:

Pro Thr Gln Tyr Pro Pro Gly Arg
1               5

(2) INFORMATION FOR SEQ ID NO: 191:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 191:

Thr Gln Tyr Pro Pro Gly Arg Gly
1               5

(2) INFORMATION FOR SEQ ID NO: 192:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 192:

Gln Tyr Pro Pro Gly Arg Gly Thr
1               5

(2) INFORMATION FOR SEQ ID NO: 193:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 193:

Tyr Pro Pro Gly Arg Gly Thr Pro
1               5

(2) INFORMATION FOR SEQ ID NO: 194:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 194:

Pro Pro Gly Arg Gly Thr Pro Pro
1               5

(2) INFORMATION FOR SEQ ID NO: 195:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 195:

Pro Gly Arg Gly Thr Pro Pro Pro
1               5

(2) INFORMATION FOR SEQ ID NO: 196:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 196:

Gly Arg Gly Thr Pro Pro Pro Pro
1               5

(2) INFORMATION FOR SEQ ID NO: 197:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 197:

Arg Gly Thr Pro Pro Pro Pro Val
1               5

(2) INFORMATION FOR SEQ ID NO: 198:

(i) SEQUENCE CHARACTERISTICS:
        (A) LENGTH: 8 amino acids
        (B) TYPE: amino acid
        (C) STRANDEDNESS: single
        (D) TOPOLOGY: linear

```
    (ii) MOLECULE TYPE: peptide (xi) SEQUENCE DESCRIPTION: SEQ ID NO: 198:

Gly Thr Pro Pro Pro Val Gly
1               5

(2) INFORMATION FOR SEQ ID NO: 199:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 199:

Pro Pro Pro Pro Val Gly Arg Ala
1               5

(2) INFORMATION FOR SEQ ID NO: 200:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 200:

Ile Met Ala Pro Pro Pro Gly Met
1               5

(2) INFORMATION FOR SEQ ID NO: 201:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 201:

Met Ala Pro Pro Pro Gly Met Arg
1               5

(2) INFORMATION FOR SEQ ID NO: 202:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 202:

Ala Pro Pro Pro Gly Met Arg Pro
1               5

(2) INFORMATION FOR SEQ ID NO: 203:

(i) SEQUENCE CHARACTERISTICS:
        (A) LENGTH: 8 amino acids
        (B) TYPE: amino acid
        (C) STRANDEDNESS: single
        (D) TOPOLOGY: linear
```

```
    (ii) MOLECULE TYPE: peptide (xi) SEQUENCE DESCRIPTION: SEQ ID NO: 203:

Pro Pro Gly Met Arg Pro Pro Met
1               5

(2) INFORMATION FOR SEQ ID NO: 204:

(i) SEQUENCE CHARACTERISTICS:
         (A) LENGTH: 8 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO: 204:

Pro Pro Ala Arg Gly Thr Pro Ile
1               5

(2) INFORMATION FOR SEQ ID NO: 205:

(i) SEQUENCE CHARACTERISTICS:
         (A) LENGTH: 8 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO: 205:

Ile Gly Met Pro Pro Pro Gly Met
1               5

(2) INFORMATION FOR SEQ ID NO: 206:

(i) SEQUENCE CHARACTERISTICS:
         (A) LENGTH: 8 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO: 206:

Gly Met Pro Pro Pro Gly Met Asx
1               5

(2) INFORMATION FOR SEQ ID NO: 207:

(i) SEQUENCE CHARACTERISTICS:
         (A) LENGTH: 6 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO: 207:

Pro Pro Pro Gly Met Asx
1               5

(2) INFORMATION FOR SEQ ID NO: 208:

(i) SEQUENCE CHARACTERISTICS:
         (A) LENGTH: 8 amino acids
         (B) TYPE: amino acid
         (C) STRANDEDNESS: single
```

```
            (D) TOPOLOGY: linear (ii) MOLECULE TYPE: peptide (xi) SEQUENCE DESCRIPTION: SEQ ID NO: 208:

Met Pro Pro Pro Gly Met Arg Pro
1               5

(2) INFORMATION FOR SEQ ID NO: 209:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 209:

Pro Pro Gly Met Arg Pro Pro Pro
1               5

(2) INFORMATION FOR SEQ ID NO: 210:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 210:

Met Arg Pro Pro Pro Pro Gly Ile
1               5

(2) INFORMATION FOR SEQ ID NO: 211:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 211:

Arg Pro Pro Pro Pro Gly Ile Arg
1               5

(2) INFORMATION FOR SEQ ID NO: 212:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 212:

Pro Pro Pro Gly Ile Arg
1               5

(2) INFORMATION FOR SEQ ID NO: 213:

(i) SEQUENCE CHARACTERISTICS:
            (A) LENGTH: 8 amino acids
            (B) TYPE: amino acid
```

```
        (C) STRANDEDNESS: single
        (D) TOPOLOGY: linear (ii) MOLECULE TYPE: peptide (xi) SEQUENCE DESCRIPTION: SEQ ID NO: 213:

Pro Pro Pro Pro Gly Ile Arg Gly
1               5

(2) INFORMATION FOR SEQ ID NO: 214:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 214:

Pro Pro Gly Ile Arg Gly Pro Pro
1               5

(2) INFORMATION FOR SEQ ID NO: 215:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 215:

Arg Gly Pro Pro Pro Pro Gly Met
1               5

(2) INFORMATION FOR SEQ ID NO: 216:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 216:

Gly Pro Pro Pro Pro Gly Met Arg
1               5

(2) INFORMATION FOR SEQ ID NO: 217:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 217:

Pro Pro Pro Pro Gly Met Arg Pro
1               5
```

(2) INFORMATION FOR SEQ ID NO: 218:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 218:

Pro Pro Gly Met Arg Pro Pro Arg
1               5

METHODS AND REAGENTS FOR DIAGNOSIS OF AUTOANTIBODIES

This is a divisional of U.S. Ser. No. 07/867,819 filed on Apr. 13, 1992 now U.S. Pat. No. 6,897,287, by John B. Harley for "Methods and Reagents for Diagnosis of Autoantibodies", which is a continuation-in-part of U.S. Ser. No. 07/648,205 filed Jan. 31, 1991 now abandoned by John B. Harley for "Assays and Treatments for Autoimmune Diseases", which is a continuation-in-part of U.S. Ser. No. 07/472,947 entitled "Assays and Treatments for Autoimmune Diseases" filed Jan. 31, 1990 by John B. Harley, now abandoned.

The United States government has rights in this invention by virtue of grants from the National Institutes of Health AR39577, AI24717, AI21568, AI31584 and AR01844, and the Veteran's Administration.

BACKGROUND OF THE INVENTION

This invention is in the area of the prevention, diagnosis and treatment of autoimmune diseases, especially systemic lupus erythematosus.

Systemic lupus erythematosus (SLE) is similar to many other disorders in which autoantibodies are found and thought to be important in etiology and pathogenesis. SLE can be grouped with those diseases that commonly have autoantibodies present but for whom a central role of autoantibody in pathogenesis leading to clinical expression has yet to be fully established or accepted. Other such diseases include Sjogren's syndrome, rheumatoid arthritis, juvenile onset diabetes mellitus, primary biliary cirrhosis, Wegener's granulomatosis, inflammatory bowel disease, and many others.

Typically, autoimmune diseases present with a wide array of symptoms and clinical signs. The production of circulating autoantibodies to ribonucleoprotein complexes (RNPs) is a unifying characteristic of some of the rheumatic autoimmune diseases. The most common antigens in SLE and closely related disorders include: Ro/SSA, La/SSB, nRNP and Sm. Initially, these antibodies were found using double immunodiffusion, but more recently sensitive solid phase assays have been developed to quantitate the autoantibodies.

The Ro/SSA RNA-protein particle has been found to be a constituent of all human cells evaluated to date. Approximately half of Sjogren's syndrome (SS) and systemic lupus erythematosus (SLE) patients have anti-Ro/SSA precipitins. Approximately 75% of patients with subacute cutaneous lupus erythematosus or complement component C2 deficiency with SLE have anti-Ro/SSA precipitins. Over 80% of mothers of newborns with neonatal lupus dermatitis or complete congenital heart block have this autoantibody. As many as 5% of patients with rheumatoid arthritis, polymyositis, and progressive systemic sclerosis have anti-Ro/SSA, as reported by R. M. Bernstein, et al., *Mol. Biol. Med.* 2:105-120 (1984); and J. B. Harley and K. K. Gaither, *Autoantibodies. In Rheumatic Disease Clinics of North American: Systemic Lupus Erythematosus* 14:1, 43-56 (1988).

Autoantibodies to the La/SSB ribonucleoprotein antigen are also found in patients with SS and SLE, as reported by Alspaugh, et al., *Arthritis Rheum.* 19:216 (1976) and Mattioli, et al., *Arthritis Rheum.* 17:421 (1974). In addition, these antibodies as reported by Horsfall, et al., *J. Autoimmunity* 4:165 (1991), thought to be pathogenic to the fetus during pregnancy in some mothers who have anti-La/SSB autoantibodies, where they are associated, along with anti-Ro/SSA, with complete congenital heart block (CCHB).

It has been an issue of intensive debate as to whether the many autoantibodies found in systemic lupus erythematosus and related diseases represent an antigen specific or a polyclonal, antigen non-specific response. Evidence that autoantibodies are important in the expression of SLE and related syndromes is convincing. Specific depletion in a heart block neonate (Harley, J. B., et al., *Arthritis Rheum.* 28:1321-1325 (1985)) and specific anti-Ro/SSA immunoglobin deposition in human skin (Lee, L. A., et al., *J. Clin. Invest.* 83:1556-1562 (1989)) have been demonstrated. Specific concentration of anti-Ro/SSA has been shown in the immunoglobulin of renal eluates from kidneys affected by lupus nephritis (Maddison, P. J. and Reichlin, M. *Arthritis Rheum.* 22:858-863 (1979)). Anti-Ro/SSA has been found to be specifically concentrated in a parotid gland of a patient with Sjogren's syndrome and primary biliary cirrhosis (Penner, E. and Reichlin, M. *Arthritis Rheum.* 25:1250-1253 (1982)). Observations that infants with transplacentally acquired maternal IgG develop neonatal lupus dermatitis and/or complete congenital heart block (Harley, J. B. and Gaither, K. K.: *Autoantibodies. In Rheumatic Disease Clinics of North America: Systemic Lupus Erythematosus* 14:1, 43-56 (1988)) strongly suggests that maternal autoantibody (anti-Ro/SSA or anti-La/SSB) transported across the placenta is a critical component required, but not sufficient, for these clinical problems.

The Ro/SSA family of proteins has now been shown to have several molecular forms which are operationally defined by the molecular weight of the antigen identified. A major form has an apparent molecular weight of 60 kiloDaltons (kD). This protein is associated with one of four hY RNAs. Recently, two additional proteins bound by anti-Ro/SSA sera have been identified by M. D. Rader, et al., *J. Clin. Invest.* 83:1556-1562 (1989), with molecular weights of 52 kD and 54 kD. A 48 kD protein, calmodulin, has been identified as being bound by anti-Ro/SSA sera (McCauliffe, et al., *J. Clin. Invest.* 85:1379-1391 (1990)). The La/SSB protein, a 48 kD peptide, as described by J.C. Chambers and J. D. Keene, *Proc. Natl. Acad. Sci. USA* 82:2115-2119 (1985), is also a member of this group of autoantibodies, and binds small RNAs with a polyuridine terminus, as reported by J. E. Stephano, *Cell* 36:145-154 (1984). La/SSB is bound by a third of the anti-Ro/SSA precipitin positive sera. The La/SSB protein has been purified from a variety of tissue sources and shown to be a 46 to 50 kD monomeric phosphoprotein, as reported by Habets, et al., *EMBO J.* 2:1625 (1983) and Venables, et al., *Clin. Exp. Immunol.* 54:731 (1983). It associates with RNA polymerase III transcripts, as reported by Lerner, et al., *Proc. Natl. Acad. Sci. USA.* 76:5495 (1979) and Steitz, et al., *Cold Spring Harbor Symposium Quant. Biol.* 47:893 (1983), and may function as a termination factor for this enzyme, as reported by Gottlieb, et al., *EMBO J.* 8:841 (1989). A nucleic acid dependent ATPase/dATPase enzymatic activity has also been attributed to La/SSB by Bachmann, et al., *Cell* 60:85 (1990).

Anti-Sm antibodies are frequently associated with SLE. These autoantibodies precipitate snRNP containing the U1, U2, U4/U6 and U5 RNA. These complexes form the spliceosome and splice heterogenous nuclear RNA, as reported by Sharp, *Science* 235:766 (1987) and Maniatis and Reed, *Nature* 325:673 (1987). Anti-Sm antibodies are directed against one or a combination of six polypeptides: B (26 kDa), B' (27 kDa), D (13 kDa), E/F (11 kDa doublet) and G (less than 10 kDa).

Nearly all rheumatic disease patients who form an anti-Sm precipitin in Ouchterlony immunodiffusion have or eventually develop an anti-nRNP precipitin, as reported by Fisher, et al., *Arthritis Rheum.* 28:1348 (1985). Anti-Sm and anti-nRNP precipitins form a line of partial identify in Ouchterlony immunodiffusion, as discussed by Mattioli and Reichlin, *J. Immunol.* 110:1318 (1973). The basis for this partially shared antigenicity is explained by the composition of the U snRNP particles. The antigen for the anti-nRNP precipitin are the 70 kD, A, and C peptides that are unique to the U1 snRNP, B/B' and D peptides are also found on the U1 snRNP. The B/B' and D Ag, but not the 70 kDa, A or C, are found in the U2, U4/U6 and U5 snRNP. Hence, both anti-Sm and anti-nRNP bind anti-U1 snRNP activity, but only anti-Sm binds U2, U4/U6, and U5 snRNP.

U.S. Ser. No. 07/648,205 filed Jan. 31, 1991 by John B. Harley for "Assays and Treatments for Autoimmune Diseases", and U.S. Ser. No. 07/472,947 entitled "Assays and Treatments for Autoimmune Diseases" filed Jan. 31, 1990, described a specific method to identify the etiologic or antigenic agent responsible for the production of autoantibodies characteristic of a particular disorder. The antigen is first isolated, using, for example, autoantibodies isolated from one or more patients. The antigen is then divided into overlapping short amino acid sequences, preferably twenty amino acids or less, most conveniently octapeptides. The sequences having the greatest reactivity with the autoantibodies are identified and then compared with all known amino acids sequences using the available computer data bases. The protein having the maximum number or proportion of sequences homologous to the sequences of greatest reactivity with the autoantibodies is among the likeliest candidate of the known sequenced proteins for the etiological agent or immunogen. Once the etiological agent and antigenic sequences are known, it is possible to design assays and reagents for the diagnosis and treatment of patients having either the etiological agent and/or autoantibodies.

The examples in the earlier applications used peptides derived from the sequence for the 60 kDa Ro/SSA protein and La/SSB, which were reactive with antisera from SLE and SS patients.

It is therefore an object of the present invention to provide additional diagnostic reagents for identifying and classifying individuals previously exposed to a particular immunogen or expressing autoantibodies reactive with Ro/SSA, La/SSB, nRNP, or Sm B/B' polypeptides, or the epitopes (or their immune equivalent) eliciting production of the autoantibodies.

It is a still further object of the present invention to provide methods and compositions for identifying and treating autoimmune disorders, such as Systemic Lupus Erythematosus and Sjogren's syndrome.

SUMMARY OF THE INVENTION

A number of octapeptides have been generated from the sequences encoding the 60 kDa Ro/SSA peptide, the La/SSB autoantigen, the 70 kD nuclear ribonucleoprotein (nRNP), and the Sm B/B' polypeptide, which represent linear epitopes for autoantibodies present in the sera of SLE and SS patients.

For example, the most important antigenic peptides derived from Sm B/B' are (29) GTFKAEDK (SEQ IP NO:1), (45) CDEFRKIKPKNAKQP (SEQ ID NO:2), (94) RVPLAGAA (SEQ ID NO:3), (101) AGG-PGVGRAAGRGVPAG (SEQ B) NO:4), (125) AGLAG-PVRGVGGPSQ (SEQ ID NO:5), (140) QVMT-POGRGTVA (SEQ ID NO:6), (165) PTQYPPGRGTPPPPV (SEQ ID NO:7), (174) TPPPPVGRATPPPGI (SEQ ID NO:8), (184) PPPGIMAP (SEQ ID NO:9), (189) MAPP-PGMIRPPM (SEQ ID NO:10), (202) PIGLPPARGTPIG-MPP (SEQ ID NO:11), (212) PIGMIPPPG (SEQ ID NO:12), (221) RPPPPGTRGPP (SEQ ID NO:13), and (228) RGPPPPGMIRPPR (SEQ ID NO:14). Additional reactive peptides can be derived from (30) TFKAFDKWVI (SEQ ID NO:15), (83) EGPPPKDT (SEQ ID NO:16), (88) KDT-GIARV (SEQ ID NO:17), AND (120) IPQAPAGLAG (SEQ ID NO:18). These were determined by binding studies. PPPGMRPP (SEQ ID NO:123) is especially antigenic and is repeated three times in the sequence of B/B'. The antigenicity of other peptides was determined and include the shorter peptides PPPGMRP (SEQ ID NO:124) and PPPGMR (SEQ ID NO:125). Substitution studies were also done. All 19 of the other common naturally occurring amino acids are substituted for an amino acid in a particular position. For example, the arginine in position six of PPPG-MIRPP (SEQ ID NO:123) can be substituted with: F, G, H, I, K, S, T, V, W and Y.

These peptides are useful in solid phase assays for patients characterized by the presence of these autoantibodies, and can be used to categorize patients as to the likelihood of developing certain conditions associated with SLE. The peptides are also potentially useful in treatment of these patients using immobilized peptide to remove autoantibody, to block binding of the autoantibodies with patient molecules reactive with the autoantibodies, or as a component of a vaccine.

EXAMPLE 1

Figure 1:
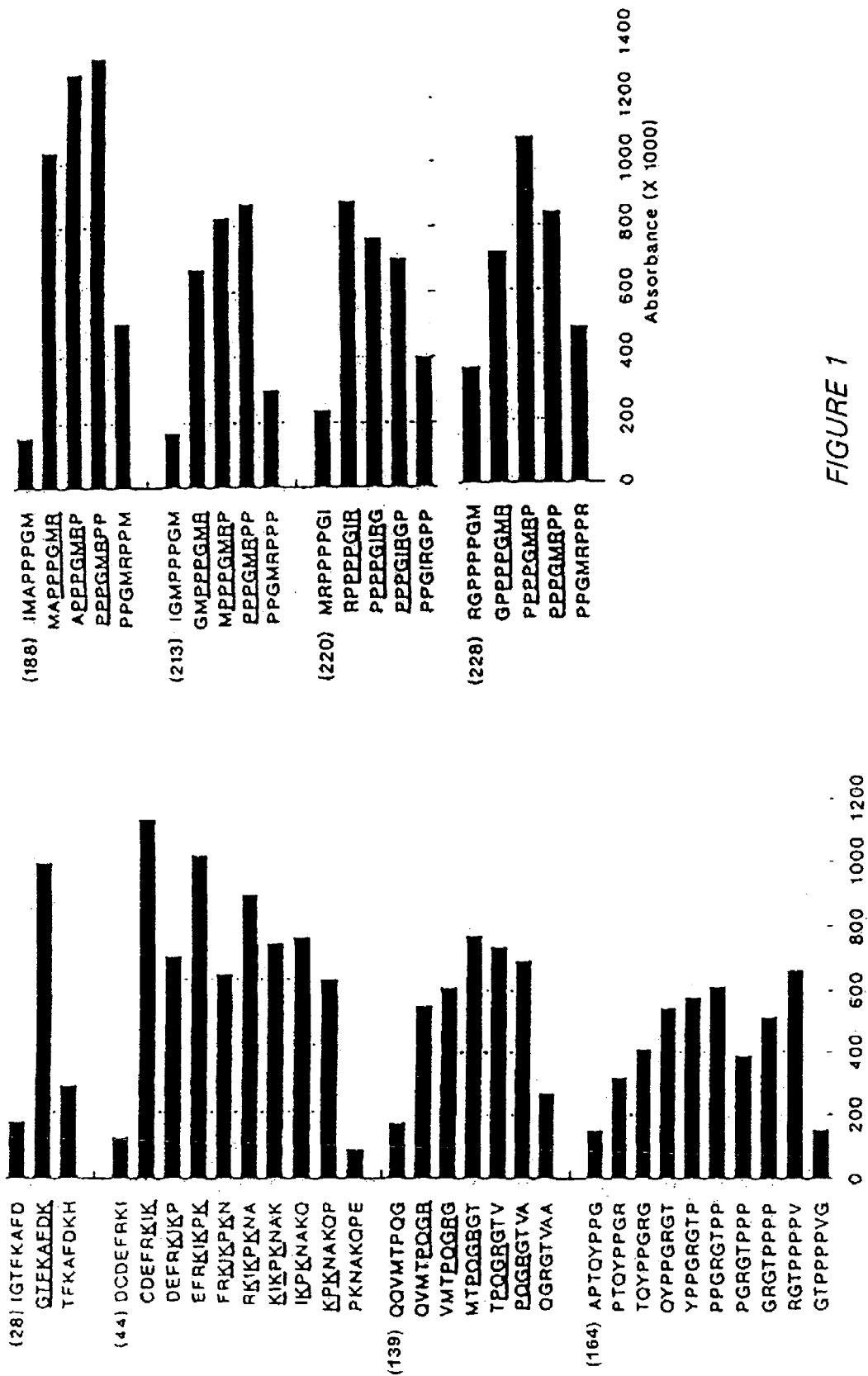
FIG. 1 graphs the antigenic regions of Sm B/B', with the octapeptides binding with an absorbance greater than 0.50, and their surrounding octapeptides. The following octapeptides are substituted with: F, G, H, I, K, S, T, V, W, and Y. studied: IGTFKAFD (SEQ ID NO:168), GTFKAFDK (SEQ ID NO:1), TFKAFDKH (SEQ ID NO:169), DCDEFRKI (SEQ ID NO:170), CDEFRKIK (SEQ ID NO:171), DEFRKIKP (SEQ ID NO:172), EFRKIKPK (SEQ ID NO:173), FRKIKPKN (SEQ ID NO:174), RKIKPKNA (SEQ ID NO:175), KIKPKNAK (SEQ ID NO:176), IKP-KNAKQ (SEQ ID NO:177), KPKNAKQP (SEQ ID NO:178), PKNAKQPE (SEQ ID NO:179), QQVMTPQG (SEQ ID NO:182), QVMTPQGR (SEQ ID NO:183), VMT-PQGRG (SEQ ID NO:184), MTPQGRGT (SEQ ID NO:185), TPQGRGTV (SEQ ID NO:186), PQGRGTVA (SEQ ID NO:187), QGRGTVAA (SEQ ID NO:188), APTQYPPG (SEQ ID NO:189), PTQYPPGR (SEQ ID NO:190), TQYPPGRG (SEQ ID NO:191), QYPPGRGT (SEQ ID NO:192), YPPGRGTP (SEQ ID NO:193), PPGRGTPP (SEQ ID NO:194), PGRGTPPP (SEQ ID NO:195), GRGTPPPP (SEQ ID NO:196), RGTPPPPV (SEQ ID NO:197), GTPPPPVG (SEQ ID NO:198), IMAP-PPGM (SEQ ID NO:200), MAPPPGMR (SEQ ID NO:201), APPPGMRP (SEQ ID NO:202), PPPGMRPP (SEQ ID NO:123), PPGMRPPM (SEQ ID NO:203), IGNIPPPGM (SEQ ID NO: 205), GMPPPGMR (SEQ ID NO:206), MPP-PGMRP (SEQ ID NO:208), PPPGMRPP (SEQ ID NO:123), PPGMRPPP (SEQ ID NO:209), MRPPPPGI (SEQ ID NO:210), RPPPPGTR (SEQ ID NO:211), PPPPGIRG (SEQ ID NO:213), PPPGIIRGP (SEQ ID NO:127), PPGIIRGPP (SEQ ID NO:214), RGPPPPGM (SEQ ID NO:215), GPP- PPGMR (SEQ ID NO:216), PPPPGMRP (SEQ ID NO:217), PPPGMRPP (SEQ ID NO:123), PPGMIRPPR (SEQ ID NO:218)

Identification of Linear Epitopes of the La/SSB Autoantigen

Patients and Methods

Peptide Synthesis. The La/SSB amino acid sequence as predicted from the nucleotide sequence of cDNA clones was as reported by Chambers, et al., *J. Biol. Chem.* 263:18043 (1988) and Sturgess, et al., *J. Immunol.* 140:3212 (1988), the teachings of which are incorporated herein. The presumably complete 408 amino acid LaISSB peptide sequence was used to construct simultaneously sequential octapeptides, each overlapping its neighbor by seven amino acids, on polystyrene pins. The entire amino acid sequence of the LaISSB protein was synthesized on five blocks of 96 pins in an 8×12 format. Onto each pin block, three identical positive control octapeptides were synthesized with the sequence EYRKKMDI (SEQ ID NO:2 19), which represents a major epitope from the carboxyl terminal sequence of the human 60 kD Ro/SSA protein. Incubating dilutions of anti-Ro/SSA reference serum on these control pins during each assay made comparisons possible among plates and between assays.

Solid Phase Anti-peptide Assay. All steps were carried out by immersing the pin blocks into microtiter plate wells. Pins were incubated in blocking buffer (1% bovine serum albumin (BSA) in phosphate buffered saline (PBS), pH 7.2) for 1 h at room temperature and then in 1:100 dilutions of sera in diluent (1% BSA and 0.05% Tween in PBS) overnight at 40° C. in humidified containers. Pin blocks were washed four times with wash buffer (0.05% Tween in PBS) for 10 min with agitation and then immersed for 1 h at room temperature in affinity purified goat anti-human-chain specific antibody conjugated to alkaline phosphatase (Sigma Chemical Co., St. Louis, Mo.) diluted 1:1000 in diluent. After washing as above, pins were incubated in para-nitrophenyl phosphate solution at 37° C. for 2 h. Color development was read at 410 nm on a Dynatech MR5000 ELISA plate reader.

Regeneration of Pins. After substrate development, blocks of pins were incubated in a 50-60° C. sonicating water bath containing freshly prepared 1% sodium dodecyl sulfate and 0.1% 2-mercaptoethanol for 1 h. They were then rinsed twice in distilled water, pre-heated to 50-60° C., and finally immersed in boiling methanol for 2 min prior to air drying.

Expression of Results. Variation within and among assays was standardized by normalizing Ro/SSA peptide positive control pins present on each block, which had been incubated with anti-Ro/SSA reference serum at a dilution of 3:1000, to a constant value of 0.175 at $A_{410}$. All absorbance data was thus normalized by multiplication with the conversion factor $A_{obs}/0.175$, where $A_{obs}$ is the observed $A_{410}$ given by the Ro/SSA control pin incubated with 3:1000 anti-Ro/SSA reference serum for any given assay. Absorbance for each octapeptide was plotted using a spreadsheet program (AOK.abc Version 2.4) on a VAX 8250/VMS computer.

Samples. Sera from five normal, healthy donors and ten patients with primary SS and/or SLE were screened by pin ELISA for antibodies binding to the La/SSB octapeptides. Eight of these ten patients had both anti-Ro/SSA and anti-La/SSB precipitin forming autoantibodies, and seven of these eight had borne children with congenital heart block (CCHB). Two patients had antibodies to Ro/SSA alone. Anti-La/SSB antibodies were affinity purified from the sera of two patients on La/SSB cross-linked immunosorbents as described by Horsfall, et al., *J. Immunol. Meth.* 104:43 (1987).

Assessment of Linear Sequence Epitopes. Background binding was defined by the total average reactivity ($A_{410}$) of five normal sera to the entire La/SSB sequence (O.D.=0.333±0.128 standard deviation). Regions of reactivity greater than or equal to 3.5 standard deviations above background binding (equivalent to 0.9998 of the normal distribution) and bound by at least three patient sera were taken to represent possible La/SSB epitopes. Epitopes were numbered in order from most to least reactive. Operationally, this was defined first by numbers of patients binding greater than or equal to 3.5 standard deviations above the normal mean as a measure of the degree of conservation between sera. As a secondary criterion, the average magnitude of peak reactivity among patients in the region of the putative epitope was used to rank epitopes having equal numbers of patient sera binding. In some cases an epitope could be a single octapeptide and in others a broad region of reactivity across several octapeptides was observed. In some of these latter cases, more than one putative epitope was identified.

Results

Binding of Anti-La/SSB Antibodies to La/SSB Octapeptides. All eight anti-La/SSB positive patient sera have strongly bound selected La/SSB Octapeptides, which span the entire sequence from the amino-terminal to the carboxyl-terminal regions. Normal sera also bind, but at a much reduced level. Sera lacking anti-La/SSB antibodies, though possessing high titers of other autoantibodies, have also shown low reactivity to the La/SSB sequence, consistent with a background response. Goat anti-human gamma-chain specific antibody conjugate used in these studies does not significantly bind to the octapeptides in the absence of human serum.

Epitopes Defined by Anti-La/SSB Sera from Patients. Positive reactivity has been defined as that greater than or equal to 3.5 standard deviations above the mean reactivity of five normal sera to overlapping octapeptides from the entire La/SSB sequence. Those regions which have been recognized by three or more anti-La/SSB sera have been defined as possible epitopes in this study, although regions reactive with one or two autoimmune sera may also constitute epitopes.

No epitope has been bound by all eight sera tested; however, 13 of the 18 epitopes defined in this way have been bound by at least four sera. In addition, peak reactivity within each epitope tends to vary among the patient sera, reflecting individual responses. Thus, although three patients have bound octapeptides of epitope 18, their greatest binding has not been found to occur with the same octapeptide. Control sera also have minimal, though positive, binding to the La/SSB sequence by this criterion. More importantly, however, two other autoimmune sera with no detectable anti-La/SSB antibodies do not bind any octapeptide from the La/SSB sequence by a magnitude of 3.5 standard deviations above the mean of the normal sera.

Epitopes have been subsequently numbered from greatest to least, taking first into account the number of sera reacting, and second the relative magnitude of the responses, as shown in Table I. Some of these epitopes correspond to areas of high antigenic index or hydrophilicity as predicted by Kyte and Doolittle plots, *J. Mol. Biol.* 157:105 (1982).

TABLE 1

La/SSB autoepitopes

| Number | Position | Sequence | |
|---|---|---|---|
| 1 | 136-153 | QVLNIQMRRTLHKAFKGS | (SEQ ID NO: 19) |
| 2 | 17-37 | ICHQIEYYFGDGNLPRDKFLK | (SEQ ID NO: 20) |
| 3 | 46-57 | WVPLEIMIKFNR | (SEQ ID NO: 21) |
| 4 | 86-97 | KTKIRRSPSKPL | (SEQ ID NO: 22) |
| 5 | 56-67 | NRLNRLTTDFNVIVE | (SEQ ID NO: 23) |
| 6 | 257-269 | GEIKWIDFVRGAK | (SEQ ID NO: 24) |
| 7 | 325-344 | SLNKWKSKGRRFKGKGKGNK | (SEQ ID NO: 25) |
| 8 | 292-303 | GNLQLRNKEVTW | (SEQ ID NO: 26) |
| 9 | 154-162 | IFVVFDSIE | (SEQ ID NO: 27) |
| 10 | 176-190 | KETDLLILFKDDYFA | (SEQ ID NO: 28) |
| 11 | 104-120 | YKNDVKNRSVYIKGFPT | (SEQ ID NO: 29) |
| 12 | 63-71 | TDFNVIVEA | (SEQ ID NO: 30) |
| 13 | 270-280 | EGIILFKEKAK | (SEQ ID NO: 31) |
| 14 | 354-367 | KVQFQGKKTKFASD | (SEQ ID NO: 32) |
| 15 | 246-253 | REDLHILF | (SEQ ID NO: 33) |
| 16 | 232-239 | CLLKFSGD | (SEQ ID NO: 34) |
| 17 | 379-386 | TGPVKRAR | (SEQ ID NO: 35) |
| 18 | 200-209 | KVEAKLRAKQ | (SEQ ID NO: 36) |

Position refers to amino acids in the La/SSB sequence as numbered from the N terminus. Epitopes are defined as having reactivity of at least 3.5 S.d. above background in at least three anti-La/SSB patient sera. Epitopes are numbered from greatest to least in order of the extend of binding. Octapeptides of each putative epitope with the greatest binding are underlined. In situations in which two octapeptides within a particular epitope have very similar binding, both are underlined.

Binding of Affinity Purified Anti-La/SSB Antibodies.

Anti-La/SSB antibodies from two patients have been affinity purified on La/SSB cross-linked immunosorbents. The affinity enriched anti-La/SSB preparation from patient E11 is specifically increased in anti-La/SSB binding activity relative to the serum from which it was prepared. The affinity enriched preparation binds 17 of the 18 previously identified epitopes, the exception being epitope 17 (octapeptide 379); however, this preparation does bind octapeptides adjacent to epitope 17, particularly octapeptides 380 and 382. Those putative epitopes in which the binding is most enriched include epitopes 2, 3, 6, 9, 10, 12, 13 and 15. These same epitopes appear enriched whether peak or average reactivities for each putative epitope are compared. Essentially the same results have been obtained from an affinity enriched preparation of the anti-La/SSB from a second patient. This demonstration of enhanced binding with increased anti-La/SSB specific activity is powerful evidence that at least these peptide sequences represent linear epitopes of the anti-La/SSB autoimmune response.

Reproducibility of La/SSB Pin ELISA.

The reproducibility of anti-Ro/SSA reference serum binding to the Ro/SSA octapeptide (EYRKKMDI) (SEQ ID NO:219) positive control pins has been followed throughout the study, giving an average standard deviation between assays of 14.0% and 16.3% for pins incubated in 1:100 and 3:100 anti-Ro/SSA reference serum, respectively. Sera with and without anti-LaISSB antibodies have also given equally consistent results when repeated in the pin ELISA.

Shared Sequences with Cardiac related Proteins. Consecutive amino acid sequence identity is shared between the heavy chain of human cardiac β-myosin and three linear regions in the La/SSB sequence, two of which coincide with La/SSB epitopes. Within epitopes 13 (La/SSB amino acids 277 through 280), a four amino acid sequence is shared with cardiac β-myosin (sequence residues 453 through 456), while there is a shared pentapeptide within epitope 18 (204 through 208) and cardiac β-myosin (619 through 623). Three of five homologous sequences shared with the M6 protein of *Streptococcus pyogenes*, the bacterium associated with rheumatic heart disease, fall within the La/SSB epitopes. Specifically, two pentapeptide matches occur in La/SSB epitopes 5 (59 through 63) and 18 (203 through 207), while a tetrapeptide match is within epitope 13 (276 through 279). Strikingly, epitopes 13 and 18 also share amino acid sequence with the B 1 chain of laminin, an adherent glycoprotein found in all basement membranes, including the sarcolemmal membrane of heart. The region within epitope 13 contains two overlapping tetrapeptide matches with laminin B1 (1202 through 1205 and 1367 through 1370), coinciding with La/SSB amino acid residues 277 through 280 and 275 through 278, respectively; while La/SSB epitope 18 (202 through 207) shares a six consecutive amino acids with laminin B1 (1467 through 1472). Antibodies binding to these epitopes were found in each of the seven sera from patients who had a child with CCHB.

EXAMPLE 2

Identification of Linear Epitopes of the 60 kD Ro/SSA Protein

Peptides that represent linear epitopes for the 60 kD protein, including many originally presented in the earlier application, are shown in Table 2. These data represent the average result from seven normal sera, four anti-Ro/SSA precipitin positive sera, and the anti-Ro/SSA affinity purified autoantibody from the same four anti-Ro/SSA precipitin positive patient sera. The data has been multiplied by a constant in each case so that the magnitude of the binding could be compared at a constant IgG concentration, 100 micrograms IgG per milliliter in these results.

This study demonstrates that the anti-Ro/SSA peptide binding activity is enriched in parallel with the anti-Ro/SSA activity directed against the native molecule. The specific binding activity against both the antigenic peptides and the Ro/SSA antigen increased by about three-fold by the affinity enrichment procedure, indicating that peptide binding is part of the overall anti-Ro/SSA response.

The first and second columns of Table 2 identify the sequences bound above a threshold of $A_{410}$ of 0.3. This threshold was chosen because none of the peptides were bound by the normal sera by an average of greater than $A_{410}$=0.3. The first column in Table 2 is from the average of four anti-Ro/SSA precipitin sera and the second is from the affinity enriched anti-Ro/SSA. In the third column are the antigenic sequences from which the antigenic octapeptides are composed. The superscript asterisk "*" identifies the octapeptide number of the octapeptide with the greatest binding of any contiguous collection all with $A_{410}$ of at least 0.3. This part of the sequence is also underlined. If two octapeptides have an $A_{410}$ within 1% of each other then two octapeptide are identified with an asterisk and the amino acids contributing to both octapeptides are underlined.

TABLE 2

Average binding of four anti-Ro/SSA sera and affinity enriched anti-Ro/SSA preparations to octapeptides constructed from the sequence of the 60 Kd Ro/SSA peptide greater than $A_{410}$ of 0.3.

| Anti-Ro/SSA Sera (Octapeptide Numer) | Affinity Purified Anti-Ro/SSA (Octapeptide No.) | Sequence | |
|---|---|---|---|
| | 30* | MNRLHRFL | (SEQ ID NO: 37) |
| | 37-38* | LCFGSEGGT | (SEQ ID NO: 38) |
| 45* | 45*-48 | SEGGTYYIKEQ | (SEQ ID NO: 39) |
| | 76-78*-79 | EIKSFSQEGRT | (SEQ ID NO: 40) |
| 81-82 | 81-82* | SQEGRTTKQ | (SEQ ID NO: 41) |
| | 84*-85 | GRTTKQEPM | (SEQ ID NO: 42) |
| 106-108* | 105-108*-109 | ISTKQAAFKAVS | (SEQ ID NO: 43) |
| | 111*-112 | AFKAVSEVC | (SEQ ID NO: 44) |
| 126-130*-133 | 126-130*-133 | FTFIQFKKDLKESMK | (SEQ ID NO: 45) |
| 139*-140 | 138-139*-140* | SMKCGMWGRA | (SEQ ID NO: 46) |
| 143-145*-146 | 142-145*-146 | GMWGRALRKAIA | (SEQ ID NO: 47) |
| 165-169*-170 | 165-173*-180 | ALAVTKYKQRNGWSHKDLLRLSH | (SEQ ID NO: 48) |
| 172-173* | | | |
| 183-184* | 182-184*-185 | LLRLSHLKPSS | (SEQ ID NO: 49) |
| | 210* | HELYKEKA | (SEQ ID NO: 50) |
| 212* | 212*-213 | LYKEKALSV | (SEQ ID NO: 51) |
| 222* | 216-222* | KALSVETEKLLKYL | (SEQ ID NO: 52) |
| | 224* | KLLKYLEA | (SEQ ID NO: 53) |
| 231-234* | 229-234* | LEAVEKVKRTKDE | (SEQ ID NO: 54) |

TABLE 2-continued

Average binding of four anti-Ro/SSA sera and affinity enriched anti-Ro/SSA preparations to octapeptides constructed from the sequence of the 60 Kd Ro/SSA peptide greater than $A_{410}$ of 0.3.

| Anti-Ro/SSA Sera (Octapeptide Numer) | Affinity Purified Anti-Ro/SSA (Octapeptide No.) | Sequence | |
|---|---|---|---|
| 257*-261 | 257*-263*-271 | HLLTNHLKSKEVWKALLQEMPL | (SEQ ID NO: 55) |
| 263-264*-265*-266 | | | |
| 280*-283 | 280*-283 | ALLRNLGKMTA | (SEQ ID NO: 56) |
| | 285* | LGKMTANS | (SEQ ID NO: 57) |
| 308-313*-315*-316 | 308-313*-315*-317 | LCNEKLLKKARIHPFHI | (SEQ ID NO: 58) |
| 330-331*-339 | 330-331*-340 | TYKTGHGLRGKLKWRPDE | (SEQ ID NO: 59) |
| | 352* | ALDAAFYK | (SEQ ID NO: 60) |
| 355*-357 | 355*-367 | AAFYKTFKTVEPTGKRFLLA | (SEQ ID NO: 61) |
| 362*-365*-366 | | | |
| | 379*-381 | ASMNQRVLGS | (SEQ ID NO: 62) |
| | 398* | AMCMVVTR | (SEQ ID NO: 63) |
| | 414* | AFSDEMVP | (SEQ ID NO: 64) |
| | 420* | VPCPVTTD | (SEQ ID NO: 65) |
| | 433* | VLMAMSQI | (SEQ ID NO: 66) |
| | 445* | TDCSLPMI | (SEQ ID NO: 67) |
| 449*-450 | 447-449*-454 | CSLPMIWAQKTNTPA | (SEQ ID NO: 68) |
| 453* | | | |
| | 472*-474 | TFAGGVHPAI | (SEQ ID NO: 69) |
| 482-484*-489 | 481-484*-489 | IALREYRKKMDIPAKL | (SEQ ID NO: 70) |
| 197-201*-203 | 197-198*-205 | IVTKYITKGWKEVHEL | (SEQ ID NO: 71) |

EXAMPLE 3

Identification of Linear Epitopes of the 70 kD Nuclear Ribonucleoprotein

The sequence of the 70 kD nuclear ribonucleoprotein (nRNP) is reported by R. A. Spritz, et al., in *Nucleic Acids Res.* 24: 10373-10391 (1987), the teachings of which are incorporated herein. The data analysis is done the same as for the Ro/SSA and La/SSB antigens. Each sequence identified represents the binding of antibody to octapeptides that exceed arbitrary criteria in the solid phase assay. The identified antigenic regions are more than two standard deviations above the mean of normal sera and are bound by more than half of the patients. For the binding to the 70 kD peptide, the threshold in the assay is $A_{410}$ of 0.380. The numbers in parentheses are the sequence positions of the first amino acid in the first octapeptide that exceeds the threshold. Each identified sequence is composed of one or more octapeptides. The number of octapeptides in each sequence is the length of the sequence minus eight. The underlined part of the sequence is the octapeptide that is bound most by the patient serum. In some cases, another octapeptide is essentially equivalent but not underlined.

The antigenic sequences of the 70 kD nRNP are: (11) ALFAPRDP (SEQ ID NO:72), (65) ERMERKRREK (SEQ ID NO:73), (133) HMVYSKRSGKPRGY (SEQ ID NO:74), (161) YKHADGKKIDGRRVL (SEQ ID NO:75), (178) VERGRTVK (SEQ ID NO:76), (186) VKGWRPRR (SEQ ID NO:77), (264) RRSRSRDK (SEQ ID NO:78), (274) RRRSRERS (SEQ ID NO:79), (277) SRERSKDK (SEQ ID NO:80), (282) KDKDRDRKRRSSRSR (SEQ ID NO:81), and (355) RRSHRSER (SEQ ID NO:82).

The A peptide of nRNP has the following antigenic octapeptides: [916)](16) NLNEKIKKD (SEQ ID NO:83), (21) IKKDELKKSL (SEQ ID NO:84), (44*) LVSRSLKM-RGQAF (SEQ ID NO:85), (73) QGFPFYDKPMRI (SEQ ID NO:86), (93) IIAKMKGTF (SEQ ID NO:87), (103*) ERDRKREKRKPKS (SEQ ID NO:88), (116) QETPAT-KKA (SEQ ID NO:89), (263) ALOGFKIT (SEQ ID NO:90), and (274) AMKISFAKK (SEQ ID NO:91). The threshold defined as two standard deviations above the mean is a normalized $A_{410}$ of 0.400. the octapeptide sequences identified by a (*) are bound by a subset of the sera tested. The sequences upon which this result is based is found in Sillekens, et al., EMBO J. 6:3841-3848 (1987), the teachings of which are incorporated herein.

The C peptide of nRNP has the following antigenic octapeptides: (19) SVRKTHCSGRKITKENVKD (SEQ ID NO:92), (35) KDYYQKWM (SEQ ID NO:93), (56) AFO-QGKIPP (SEQ ID NO:94), (61) KIPPTPFS (SEQ ID NO:95), (78) PPPPSLPG (SEQ ID NO:96), (82) SLPGP-PRP (SEQ ID NO:97), (85) GPPRPGMMPA (SEQ ID NO:98), (108) PPPPGMMP (SEQ ID NO:99), (117) GPA-PGMRPP (SEQ ID NO:100), (136) PPMMRPPA (SEQ ID NO:101), and (152) PGMTRPDR (SEQ ID NO:102). The threshold for binding of these octapeptides was $A_{410}$ of 0.440. The sequence upon which this result is based is in Sillekens, et al., Nucleic Acids Res. 25:8307-8321 (1988), the teachings of which are incorporated herein.

EXAMPLE 3

Linear Epitope Mapping of an Sm B/B' Polypeptide

Autoantibodies binding the Sm B/B' peptides are commonly associated with SLE IgG antibodies binding overlapping octapeptides of Sm B/B' have been evaluated in 10 patients with anti-Sm and anti-nRNP precipitins, 5 patients with other autoimmune serology, and 4 normal human sera. Neither normal controls nor patients without an anti-Sm precipitin significantly bind any of the Sm B/B' octapeptides. All sera tested containing an anti-Sm precipitin strongly bind octapeptides from eight regions of the Sm B/B' sequence. Three of these eight regions share the same octapeptide sequences (PPPGMRPP) (SEQ ID NO:123) that are consistently the most immunoreactive octapeptides from Sm B/B'. Binding of the similar PPPGIRGP (SEQ ID NO:127), as well as binding to deletion and substitution peptides, suggest that the motif PPPG(I,M) (R,K) appears to best define this binding. PAPGMIRPP (SEQ ID NO:116) in the nRNP C peptide is as antigenic as PPPGMRPP (SEQ ID NO:123) and may provide a partial explanation for the cross-reactivity shown between Sm and nRNP autoantibodies. However, the sequence PPPGMIPP (SEQ ID NO:117) from nRNP A is not antigenic. These data define the linear sequence autoantigenicity of the Sm B/B' protein. They also demonstrate that the predominant autoimmune epitope is a proline-rich sequence from which limited variance is permitted before antigenicity is destroyed.

Two sequences of Sm B/B' have been reported. Rokeach et al., J. Biol. Chem. 264:5024 (1989) have obtained a sequence from a lymphoblastoid cell (Raji) library that is identical to a partial clone from HeLa cells, reported by Sharpe, et al., FEB Lett. 250:585 (1989) and to Sm N from a human cerebellar library reported by Schmauss, et al., Nucleic Acids Res. 17:1733 (1989). Sm B and Sm B' have very similar amino acid sequences, van Dam, et al., EMBO J. 8:3853 (1989). Indeed, it appears, that Sm B and Sm B' are alternate splicing products from a common pre-mRNA.

In this study overlapping octapeptides of the encoding regions of both Sm B/B' sequences were synthesized by solid-phase peptide synthesis. Antigenicity of each octapeptide was determined with a variety of sera from patients with SLE and normal controls.

Materials and Methods

Sera. Human sera form patients who satisfied the classification criteria of the American Rheumatism Association for SLE or normal age-matched, sex-matched controls were used in this study. Fifteen sera from lupus patients were tested. Ten of these sera tested contained antibodies that formed strong precipitin lines with both Sm and nRNP, three formed precipitin lines with only nRNP, one formed a precipitin line with Ro/SSA and La/SSB, and one formed a precipitin line with only Ro/SSA. All of these serologic findings were confirmed by appropriate molecular weight bands for the reported antigen being bound in immunoblot by the respective sera.

Solid-phase noncleavable peptide synthesis. The published sequence of Sm B/B' was used to construct all the possible overlapping octapeptides. The amino acids used for peptide synthesis had Fmoc protected primary amino groups and t-butyl (or other appropriate group) protected side chains. Overlapping octapeptides were simultaneously synthesized at the rounded ends of radiation derivatized polyethylene pins that were arranged in the format of a 96 well microliter plate (Cambridge Research Biochemicals. Cambridge, UK and Coselco Mimotopes Pty Ltd. Victoria, Australia) The active esters of Fmoc, t-butyl amino acid solutions (30 mM) were solubilized in DMF that had 10 hydroxybenzotriazole added to a final concentration of 30 mM and dispensed into the wells of a microliter plate. Each amino acid was added as determined by the 240 amino acids of the Raji Sm B/B' sequence. After 18 h of incubation, the pins were washed in DMF for 5 min. four times at 2 min each in methanol, and once again in DMF for 5 min. The Fmoc protecting groups were then removed from the newly added amino acid by a 20% piperidine/DMF bath for 30 min. These steps were repeated until all eight amino acids were added. After the final amino acid, the amino terminal groups of each peptide was acetylated by incubating the pins in a 5:2:1 (v/v/v) mixture of DMF:acetic anhydride: triethylamine for 90 min at room temperature. After this step the pins were again washed in DMF for 2 min, four times at 2 min each in methanol, and then air-dried for 10 min. Finally, side chain amino protecting groups were removed by 95:2, 5:2.5 (v/w/v) of trifluoracetic acid:phenol:ethanedithiol. Wash steps included 2 min in methylene chloride, two times at 5 min each in 5% diisopropylethylene/methylene chloride, and a final methylene chloride wash for 5 min. After drying for 10 min., pins were placed in distilled water for 2 min., transferred to a methanol bath for 18 h. and dried under vacuum for 18 h. This procedure was repeated to synthesize another set of the carboxyl-terminal 36 octapeptides to allow substantiation of the previous data. In addition other octapeptides, including the amino acid changes seen in the vanDam/Ohosone *Proc. Natl. Acad. Sci. USA* 86:4249 (1989) sequences, were also synthesized. Selected substitution and deletion sequences, along with similar sequences from other proteins, were also constructed. Control pins composed of amino acids in a random sequence were prepared that were not present in any of the Sm or nRNP antigen sequences. In addition, positive control pins were synthesized from a known reactive sequence of the La/SSB peptide.

Solid-phase cleavable peptide synthesis. Coselco Mimotopes Pty Ltd. has developed a method of producing cleavable peptides. These peptides are synthesized on polyethylene pins that contain a cleavable linker assembly that contains an additional proline-lysine-alanine sequence. After synthesizing the peptide as described above, a final 15-min sonication in 0.1% HCl (in 1:1 methanol/ddH$_2$O) is added. Pins are incubated in a solution of equal amounts of 0.1 M citrate and 0.1 M phosphate buffer at pH 3.0 for 3 h with gentle agitation. This removes all residual contaminants. Peptides are then cleaved from the pins by incubation in a 0.1 M phosphate solution at ph 7.0 that causes cyclization and formation of a diketopiperazole. These peptides were then analyzed for amino acid content. Four octapeptides were constructed as described and the correct amino acids in the proper ratios were present in all peptides tested.

Solid phase antipeptide assay. Wash steps and incubations were carried out in sealed plastic containers. Other assay steps were performed by lowering the pins into microliter plate wells. First, pins were blocked with 3% low-fat milk in PBS for 1 h at room temperature. Pins were then incubated in 1/100 dilutions of sera in 3% milk/PBS with 0.05% Tween overnight at 4° C. in humidified sealed containers. The pin blocks were then washed four times with PBS with 0.05% Tween for 10 min each with vigorous agitation. Next, each pin was incubated with anti-human gamma-chain specific IgG raised in a goat, affinity purified and conjugated to alkaline phosphatase (Jackson Immunoresearch Laboratories, West Grove, Pa.) at a 1/10,000 dilution. Paranitrophenyl phosphate disodium was used as a substrate for alkaline phosphatase and plates were read at 405 nm with a Microelisa Reader (Dynatech, Alexandria, Va.). Results for each plate were then standardized by comparison with positive control pins. The same control pins were used for all plates and were allowed to develop to a specific OD with a known concentration of a standard control sera.

After completion of an assay, pins were sonicated for 2 h in sonication buffer (40 g SDS, 4 ml β-mercaptoethanol. and 62.4 g sodium phosphate to 4 liters) to remove antibodies, conjugate, and substrate. After sonication pins were washed twice in hot water and boiled in methanol for 2 min. Pins were then allowed to air dry for a minimum of 10 min and were stored with desiccant or used for another assay.

Epitope mapping of Sm B/B'. Peptides were first screened for reactivity with anti-human IgG conjugate alone. No background was demonstrated with anti-human IgG conjugate. Four normal human sera also showed minimal background reactivity with no specific antigenic regions demonstrated. SLE patients with autoimmune serology other than anti-Sm, anti-nRNP also showed no convincing, specific reactivity with any of the octapeptides. Other rheumatic serology tested included sera which formed precipitins with Ro/SSA as well as with both Ro/SSA and LaISSB Ag. Every patient who precipitated Sm and nRNP, however, showed considerable reactivity with various regions of the Sm B/B' protein. Ten Sm, nRNP sera were tested and all had a similar pattern of binding. Considerable reactivity was demonstrated in the proline-rich, carboxyl-terminal region of the protein. A repeated motif, PPPGMRPP (SEQ ID NO:123), is found in three regions of the Sm B/B' polypeptide and is similarly antigenic in each. In addition, a closely related fourth region, PPPGIRGP (SEQ ID NO:127), is bound by all the Sm, nRNP sera tested.

Several other antigenic regions were also detected in the first and middle portions of the polypeptide. These regions were not strongly reactive in all sera tested; however, they may be important by defining the differences in the very fine specificity between individuals with an autoimmune response to the B/B' Ag.

To elucidate which amino acids are essential for reactivity the average binding surrounding each purported epitope is presented along with the sequence of each relevant octapeptide in FIG. 1. The octapeptide starting with amino acid 29, GTFKAFDK (SEQ ID NO:1), requires all eight residues for reactivity. The antigenicity of the reactive area in the region of octapeptide 45, however, appears to be based on a requirement for two lysines with an intercalated amino acid spacer. Binding is lost in octapeptides 44 and 53 when the two lysines with intercalated spacer is eliminated.

The sequence from octapeptides 140 to 145 all have moderately elevated average binding. Each shares a PQGR (SEQ ID NO:128) sequence that would appear to be critical for binding. The reactive site surrounding octapeptide 169, on the other hand, is not easily explained by a specific sequence. The repeated PPPGMRPP (SEQ ID NO:123) and the similar PPPGIRGP (SEQ ID NO:127) found at octapeptides 191, 216, 223, and 231 share the hexamer, PPPGXR (SEQ ID NO:119), where X indicates an undetermined amino acid, in all of the octapeptides with the greatest binding. This repeated motif appears to be important in the binding of anti-Sm to linear epitopes of Sm B/B'.

Figure 2A:
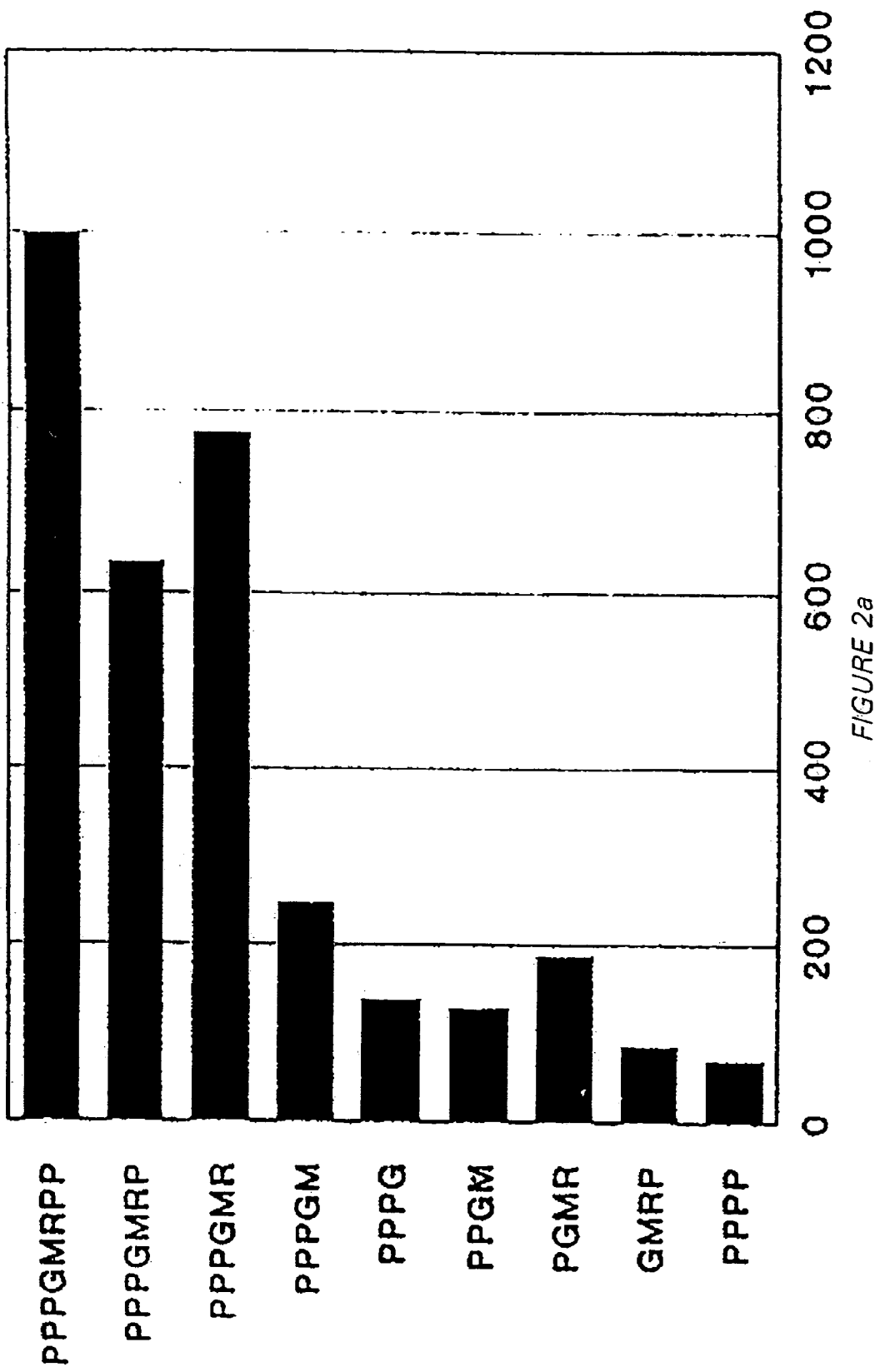
FIG. 2a, shows the decrease in binding for remov The present invention will be further understood with reference to the following non-limiting examples.

Deletion experiments with PPPGMRPP (SEQ ID NO:123). Deletion experiments of the PPPGMRP (SEQ ID NO:124)sequence demonstrated that not all eight amino acids are required for antigenicity with the six patient sera tested, as shown in FIG. 2a. Peptides were synthesized that deleted the carboxyl-terminal amino acid leaving a heptamer of PPPGMRP (SEQ ID NO:124), a hexamer of PPPGMR (SEQ ID NO:125), a pentamer of PPPGM (SEQ ID NO:129), and various tetrameres including PPPG (SEQ ID NO:130), PPGM (SEQ ID NO:131), PGMR (SEQ ID NO:132), GMRP (SEQ ID NO:133), andPPPP (SEQ ID NO:134). Binding appears to require at least the hexamer PPPGMR (SEQ ID NO:125) before the significant reactivity is lost. Greater than 60% of the reactivity to the PPPGMRPP (SEQ ID NO:123) motif is destroyed when the sixth position arginine is removed. Removal of the carboxyl terminal prolines does not appear to significantly alter binding in the six patients tested. In addition no solely poly-proline sequence tested (PPPPP (SEQ ID NO:120), PPPP (SEQ ID NO:135), PPP, PP) has shown reactivity with these sera. Six of the 10 sera containing anti-Sm and anti-nRNP were tested with these deleted peptides and gave similar results. A normal serum did not bind any of these peptides.

Figure 2B:
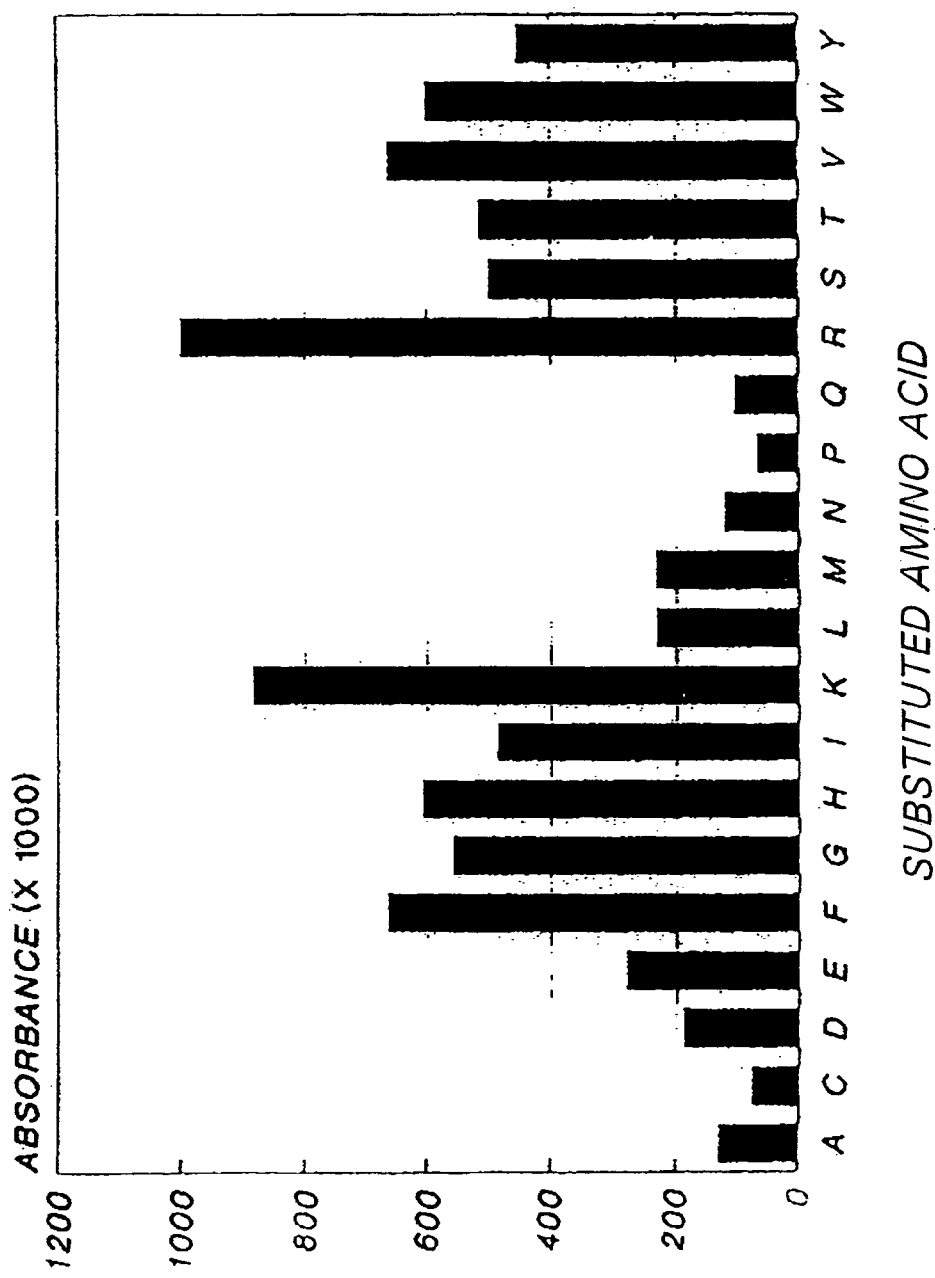
FIG. 2 graphs the results of deletion studies on the Sm B/B' epitope PPPGIVIRPP (SEQ ID NO:123)

Substitution experiments of PPPGMRPP antigenic sequence. Substitution of the arginine (R) with the other 19 naturally occurring amino acids demonstrated varying levels of reactivity with the six sera tested, as shown in FIG. 2b. Substitution of the arginine by another positively charged amino acid, lysine (K), preserves more than 75% of the original reactivity. Another subset of the nine amino acids (containing F, G, H, I, S, T, V, W, and Y) retain approximately 50 to 65% of original binding, whereas the other nine amino acids reduce binding to less than 25%.

Synthesis of various similar epitopes. Short sequences of various proteins that displayed considerable homology with the PPPGMIRPP (SEQ ID NO:123) motif were also synthesized on polyethylene pins. These sequences and their reactivity, as measured by six different patient sera with anti-Sm and anti-nRNP precipitins from the first experiments. Octapeptides from nRNP A (23), nRNP C (24), and the EBV nuclear Ag-1 (25) were prepared. The nRNP A and one nRNP C sequence showed relatively no reactivity; however, the second nRNP C sequence (PAPGMIRPP) (SEQ ID NO:116) showed over 90% of the original binding. In addition, the EBV sequence (which has five of six amino acid homology with the required antigenic portion of PPPGMIRPP) (SEQ ID NO:123)is also significantly bound by Sm, nRNIP precipitin positive patients.

All antigenic sites determined in this study require a positively charged amino acid. The size of these sites varies from two nonconsecutive basic amino acids to an entire octapeptide. The PPPGMRPP (SEQ ID NO:123) motif appears to be the major linear antigenic epitope in all Sm, nRNP sera tested; however, this sequence does not appear to be bound by sera that contain an anti-Sm precipitin in the absence of an anti-nRNP precipitin. Sm precipitin alone patients bind two regions of Sm B/B'.

The carboxyl-terminal di-proline of the PPPGMRPP (SEQ ID NO:123) motif is not required for antigenicity. Other deletion studies have also shown that the antigenicity of these autoantibodies are not specifically directed against the poly-proline regions. Peptides containing from two to six polyprolines have shown no reactivity with the sera used in this study. In addition, naturally occurring octapeptides of amino acid sequences 175-186 and 85-92 contain three or four consecutive prolines: none of these regions is antigenic. Also the very similar PPPGMIPP (SEQ liD NO:117) octapeptides does not bind to the sera precipitating Sm and nRNP.

Substitution experiments have shown that changing one amino acid can reduce reactivity of a sequence by more than 90%. Substituting the other 19 naturally occurring amino acids for the sixth amino acid, arginine (R), of the PPPGMRPP sequence has divided these amino acids into three separate groups. Lysine (K), another basic amino acid, is the only substitution that preserves an average of more than 75% of the binding. With each of the sera tested, this amino acid substitution is consistently the most reactive. However, reactivity is ablated to less than 25% with nine amino acids. This set includes the acidic amino acids and their amines, the sulfur-containing amino acids, and the hydrophobic leucine, proline, and alanine. The other nine amino acids retain part, 42 to 65%, of the original binding. Phenylalanine was consistently the most reactive of this group. Nevertheless, the ability of lysine to substitute for arginine leads to the hypothesis that a positively charged amino acid at this position is preferred for the antigenicity of this sequence.

EXAMPLE 4

Binding of Monoclonal Antibodies Against Peptide Determinants of Sm B/B'

Autoantibodies binding the Sm B and B' peptides (B/B') are commonly associated with systemic lupus erythematosus in man and in MIRL lpr/lpr mice. KSm 3 and KSm 5 were derived from an unmanipulated MThL lpr/lpr mouse using hybndoma monoclonal antibody technology. Supematants containing KSm 3 and KSm 5 monoclonal antibodies were collected from cloned murine hybndoma cell lines in RPMI 1640 with 10% fetal bovine serum, glutamine, penicillin and streptomycin. These monoclonal autoantibodies are both of the IgG2a subclass. The linear antigenic regions of these two anti-Sm B/B' murine monoclonal autoantibodies have been mapped using overlapping octapeptides. Unique epitopes are identified by each monoclonal. Monoclonal antibody KSm 5 recognizes the peptide, PPPGMRPP (SEQ ID NO:123), which is repeated three times in the Sm B polypeptide. KSm 3 binds best to two very similar, almost neighboring octapeptides, PPPGIRGP (SEQ ID NO:127) and PGIRGPPP (SEQ ID NO:121). The two monoclonals do not crossreact. Both of these regions of Sm B/B' are major areas of antigenicity for human anti-Sm autoantibodies. Amino acid deletion and substitution in antigenic octapeptides show that binding to the KSm 5 epitope is lost with only slight modification. When the arginine in the sixth position PPPGMRPP (SEQ ID NO:123) is substituted KSm 5 binding is found in an unexpected subset of octapeptides. Molecular dynamic modelling suggests that binding may be associated with a shared peptide backbone structure rather than charge or hydrophobicity of the substituted amino acid. In contrast, binding of KSm 3 to PPPGIRPP (SEQ ID NO:122) is abolished when the sixth position arginine is substituted by any other amino acid. These two murine autoantibodies bind distinct linear epitopes of Sm B/B' which are also bound by human anti-Sm B/B' autoantibodies. The bound epitopes are proline rich and contain an arginine in the fourth or sixth position. Thus, substitution at arginine and modelling experiments suggest very different mechanisms of binding for KSm 3 and KSm 5. A particular peptide backbone conformation, conferred by some amino acid sidechains at Position 6 of the octapeptide PPPGMRPP (SEQ ID NO:123), may be involved in KSm 5 binding while KSm 3 binding requires the specificity of the arginine side chain. Naturally arising autoantibodies may bind quite different features of similar peptide structures.

Substitution of either the fifth or sixth position amino acids of PPPGIRGP (SEQ ID NO:127) with all of the other nineteen naturally occurring amino acids shows unique patterns of reactivity. Substitution of the sixth amino acid arginine (R) shows that no other amino acid allows any degree of binding. When the fifth position isoleucine (I) is substituted, six of the twenty amino acids, phenylalanine (F), histidine (B) threonine (T), valine (V) and tyrosine (Y), allow over 50% of the binding shown with the original octapeptide. Of these, threonine has more reactivity than the original octapeptide.

To determine structural motif common to peptides of either antigenic group, molecular dynamic simulations were performed for selected peptides which are antigenic to KSm 5 or KSm 3. A total of 2500 structures representing a nanosecond trajectory in time were accumulated for each peptide, and analyzed by monitoring backbone dihedral angles. At least one prevalent conformer could be chosen for all peptides as observed by a stable set of backbone dihedral angles. The root mean square difference between the KSm 3 positive peptides PPPGTRGP (SEQ ID NO:127) and PGIRGPPP (SEQ ID NO:121) of 4.87 A for the backbone atoms of eight residues indicates that there is no common backbone between these two peptides.

In contrast, the binding of KSm 5 to peptides substituted for arginine (R) in the sixth position in PPPGMIRPP (SEQ ID NO:123) suggest quite different binding requirements. Amino acids with side chains, $—(CH_3)_3—NH—C—NHNH—_2$, $-CH_3$, —OH, and —H, all were roughly-equivalent in their ability to be bound by KSm 5. No feature of charge or hydrophobicity is shared by these amino acids. Also, lysine and histidine, the amino acids usually considered most similar to arginine, could not substitute and preserve binding. The possibility of a significant backbone conformation common to the native peptide PPPGMRPP (SEQ ID NO:123) off set by one or more amino acids in either direction was ruled out using OVRLAP18. The best match was found for the first few residues of the backbone with no offset. Accordingly, the conformation may play a role in binding.

Modifications and variations of the method and reagents of the present invention will be obvious to those skilled in the art from the foregoing detailed description. Such modifications and variations are intended to come within the scope of the appended claims.

We claim:

1. A method for screening patients for systemic lupus erythematosus (SLE) comprising (a) reacting a serum sample containing an autoantibody with an epitope selected from the group of Sm B/B' epitopes consisting of: IGTFKAFD (SEQ ID NO:168), TFKAFDKH (SEQ ID NO:169), GTFKAFDK (SEQ ID NO:1), TFKAFDKHM (SEQ ID NO:15), DCDEFRKI (SEQ ID NO:170), CDEFAKIK (SEQ ID NO:171), CDEFRKIKPKNAKQP (SEQ ID NO:2), EFRKIKPK (SEQ ID NO:173), RKIKPKNA (SEQ ID NO:175), KIKPKNAK (SEQ ID NO:176), IKPKNAKQ (SEQ ID NO:177), KPKNAKQP (SEQ ID NO:178), PKNAKQPE (SEQ ID NO:179), EGPPPKDT (SEQ ID NO:16), KDTGIARV (SEQ ID NO:17), RVPLAGAA (SEQ ID NO:3), AGGPGVGRAAGRGVPAG(SEQ ID NO:4), PGVGRAAG (SEQ ID NO:180), IPQAPAGLAG (SEQ ID NO:18), AGLAGPVRGVGGPSQ (SEQ ID NO:5), VRGVGGPS (SEQ ID NO:181), QQVMTPQG (SEQ ID NO:182), QVMTPQGR (SEQ ID NO:183), VMTPQGRG (SEQ ID NO:184), PQGR (SEQ ID NO:128), TPQGRGTV (SEQ ID NO:186), PQGRGTVA (SEQ ID NO:187), QGRGTVAA (SEQ ID NO:188), APTQYPPG (SEQ ID NO:189), PTQYPPGR (SEQ ID NO:190), TQYPPGRG (SEQ ID NO:191), QYPPGRGT (SEQ ID NO:192), YPPGRGTP (SEQ ID NO:193), PPGRGTPP (SEQ ID NO:194), PGRGTPPP (SEQ ID NO:195), GRGTPPPP (SEQ ID NO:196), RGTPPPPV (SEQ ID NO:197), GTPPPPVG (SEQ ID NO:198), TPPPPVGRATPPPGI (SEQ ID NO:8), PPPPVGRA (SEQ ID NO:199), PPPGIMAP (SEQ ID NO:9), IMAPPPGM (SEQ ID NO:200), MAPPPGMRPPM (SEQ ID NO:10), MAPPPGMR (SEQ ID NO:201), PPPGMR (SEQ ID NO:125), APPPGMRP (SEQ ID NO:202), PPGMRPPM (SEQ ID NO:203), PIGLPPARGTPIGMPP (SEQ ID NO:11), PPARGTPI (SEQ ID NO:204), PIGMPPPG (SEQ ID NO:12), IGMPPPGM (SEQ ID NO:205), MPPPGMRP (SEQ ID NO:208), PPGMRPPP (SEQ ID NO:209), MRPPPPGI (SEQ ID NO:210), RPPPPGIR (SEQ ID NO:211), RPPPPGIRGPP (SEQ ID NO:13), PPPGIR (SEQ ID NO:212), PPPPGIRG (SEQ ID NO:213), PPPGIRGP (SEQ ID NO:127), PPGIRGPP (SEQ ID NO:214), RGPPPPGM (SEQ ID NO:215), RGPPPPGMRPPR (SEQ ID NO:14), GPPPPGMR (SEQ ID NO:216), PPPPGMRP (SEQ ID NO:217), PPGMRPPR (SEQ ID NO:218), and (b) detecting autoantibody in the patient sample bound to said epitope.

2. The method of claim 1, wherein the epitope further comprises a compound selected from the group consisting of a dye, a fluorescent label, a chemilluminescent label, an enzyme, and a radioactive label.

3. The method of claim 1, wherein the epitope is immobilized onto a substrate.

4. The method of claim 1, further comprising predicting the prognosis of the patient based on the reactivity of the autoantibody in the patient sample with the epitope.

* * * * *